US009593329B2

(12) United States Patent
Gibson et al.

(10) Patent No.: US 9,593,329 B2
(45) Date of Patent: *Mar. 14, 2017

(54) ASSEMBLY OF LARGE NUCLEIC ACIDS

(75) Inventors: Daniel G. Gibson, Crofton, MD (US); Lei Young, Gaithersburg, MD (US); John I. Glass, Germantown, MD (US); Gwynedd A. Benders, San Diego, CA (US); J. Craig Venter, La Jolla, CA (US); Clyde A. Hutchison, III, La Jolla, CA (US); Hamilton O. Smith, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 737 days.

This patent is subject to a terminal disclaimer.

(21) Appl. No.: 12/247,126

(22) Filed: Oct. 7, 2008

(65) Prior Publication Data

US 2009/0275086 A1 Nov. 5, 2009

Related U.S. Application Data

(60) Provisional application No. 60/978,388, filed on Oct. 8, 2007, provisional application No. 60/983,549, filed on Oct. 29, 2007, provisional application No. 61/062,214, filed on Jan. 23, 2008, provisional application No. 61/023,392, filed on Jan. 24, 2008, provisional application No. 61/096,270, filed on Sep. 11, 2008.

(51) Int. Cl.
*C12N 15/10* (2006.01)
*C12N 15/81* (2006.01)

(52) U.S. Cl.
CPC ......... *C12N 15/1093* (2013.01); *C12N 15/81* (2013.01)

(58) Field of Classification Search
None
See application file for complete search history.

(56) References Cited

U.S. PATENT DOCUMENTS

| | | | |
|---|---|---|---|
| 5,976,846 | A | 11/1999 | Passmore et al. |
| 7,723,077 | B2 | 5/2010 | Young et al. |
| 7,776,532 | B2 | 8/2010 | Gibson et al. |
| 2003/0032033 | A1 | 2/2003 | Anglin et al. |
| 2003/0165946 | A1 | 9/2003 | Evans |
| 2007/0037196 | A1 | 2/2007 | Gibson et al. |
| 2007/0037197 | A1 | 2/2007 | Young et al. |

FOREIGN PATENT DOCUMENTS

| | | |
|---|---|---|
| WO | WO 98/01573 A1 | 1/1998 |
| WO | WO 00/06715 A1 | 2/2000 |
| WO | WO 00/75299 A1 | 12/2000 |
| WO | WO 03/029430 A2 | 4/2003 |
| WO | WO 2004/113534 A1 | 12/2004 |
| WO | 2007/032837 A2 | 3/2007 |
| WO | 2007/047148 A1 | 4/2007 |
| WO | WO 2009/045550 A2 | 4/2009 |

OTHER PUBLICATIONS

Cello et al., Chemical Synthesis of Poliovirus cDNA: Generation of Infectious Virus in the Absence of Natural Template, *Science*, 297:1016-1018, 2002.
Ebersol et al., "Rapid generation of long synthetic tamdem repeats and its application for analysis in human artificial chromosome formation", *Nucleic Acids Res.*, 33(15):e130, 2005.
Gibson et al., "Complete Chemical Synthesis, Assembly, and Cloning of a Mycoplasma genitalium Genome", *Science* 319:1215-1220, 2008.
Itaya et al., "Combining two genomes in one cell: Stable cloning of the Synechocystis PCC6803 genome in the Bacillus subtilis 168 genome", *PNAS* 102(44):15971-15976, 2005.
Kodumal et al., "Total synthesis of long DNA sequences: Synthesis of a contiguous 32-kb polyketide synthase gene cluster", *PNAS* 101(44):15573-15578, 2004.
Kouprina et al., "Segments missing from the draft human genome sequence can be isolated by transformation-associated recombination cloning in yeast", *EMBO Rep.*, 4(3):257-262, 2003.
Larionov et al., "Specific cloning of human DNA as yeast artificial chromosomes by transformation-associated recombination", *PNAS* 93:491-496, 1996.
Noskov et al., "Defining the minimal length of sequence homology required for selective gene isolation by TAR cloning", *Nucleic Acids Res.*, 29(6):e32, 2001.
Raymond et al., "General Method for Plasmid Construction Using Homologous Recombination", *BioTechniques* 26:134-141, 1999.
Raymond et al., "Linker-Mediated Recombinational Subcloning of Large DNA Fragments Using Yeast", *Genome Research* 12:190-197, 2002.
Smith et al., "Generating a synthetic genome by whole genome assembly: X174 bacteriophage from synthetic oligonucleotides", *PNAS* 100(26):15440-15445, 2003.
Burke et al., "Cloning of large segments of exogenous DNA into yeast by means of artificial chromosome vectors", *Science*, 236(4803):806-812 (1987).
Gibson et al., "One-step assembly in yeast of 25 overlapping DNA fragments to form a complete synthetic Mycoplasma genitalium genome", *Proc. Natl. Acad. Sci. USA.*, 105(51):20404-20409 (2008).
Kouprina et al., "Selective isolation of large chromosomal regions by transformation-associated recombination cloning for structural and functional analysis of mammalian genomes", *Methods Mol. Biol.*, 349:85-101 (2006).
Noskov et al., "A general cloning system to selectively isolate any eukaryotic or prokaryotic genomic region in yeast", *BMC Genomics*, 4(1):16, pp. 1-11 (2003).

(Continued)

*Primary Examiner* — Nancy Treptow
(74) *Attorney, Agent, or Firm* — DLA Piper LLP (US)

(57) ABSTRACT

A method to assemble any desired nucleic acid molecule by combining cassettes in vitro to form assemblies which are further combined in vivo, or by assembling large numbers of DNA fragments by recombination in a yeast culture to obtain desired DNA molecules of substantial size is described.

8 Claims, 9 Drawing Sheets

(56) References Cited

OTHER PUBLICATIONS

Shanks et al., "Saccharomyces cerevisiae-based molecular tool kit for manipulation of genes from gram-negative bacteria", *Appl. Environ. Microbiol.*, 72(7):5027-5036 (2006).

Heider, D. & Barnekow, A.: "*DNA-Based Watermarks Using the DNA-Crypt Algorithm*". BMC Bioinformatics, May 27, 2007, vol. 8, No. 176; 7 pages.

Den Dunnen, J. T. et al.: "*Reconstruction of the 2A MB Human DMD-Gene by Homologous YAC Recombination*"; Human Molecular Genetics, vol. 1:1, Apr. 1, 1992, pp. 19-28.

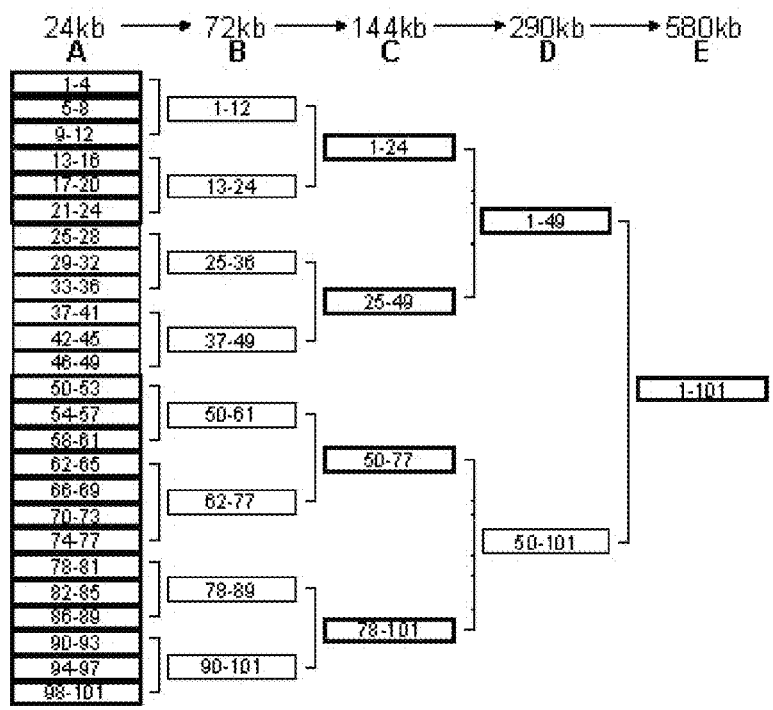
Figure 3
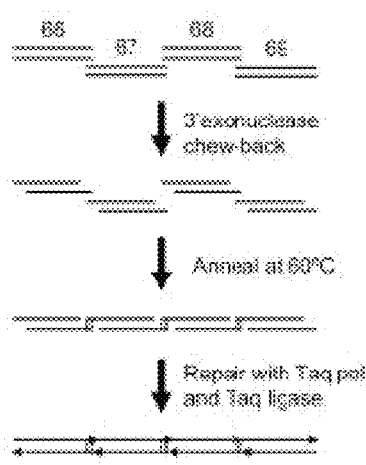
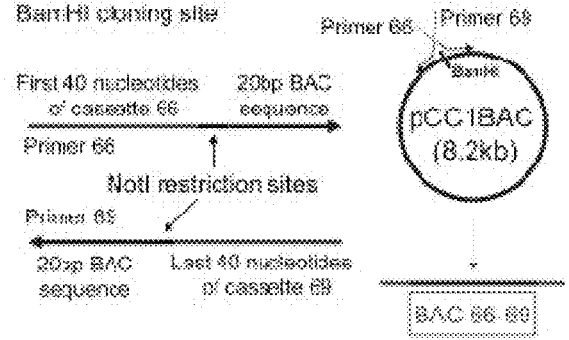
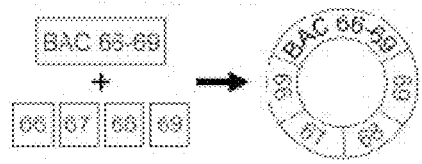
Figure 4

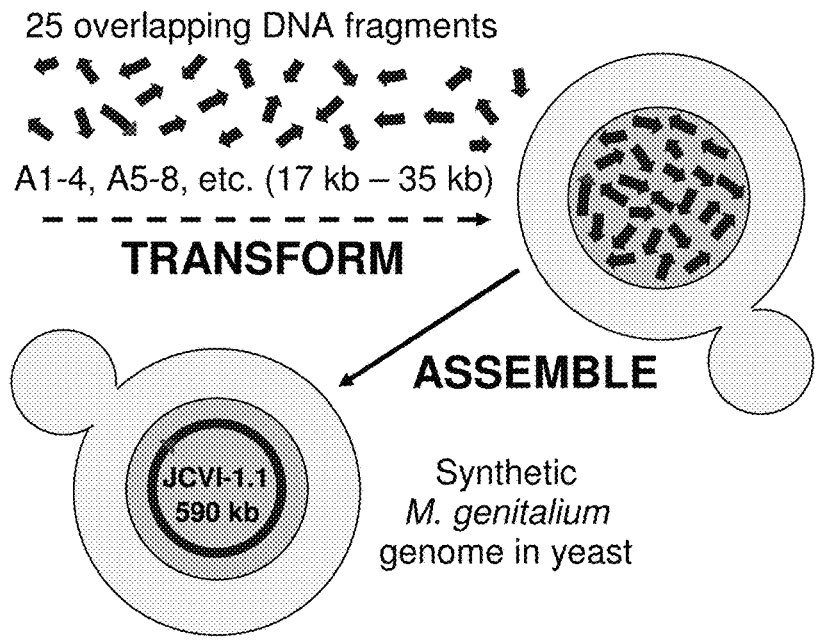
Figure 9
A
| Amplicon | a | b | c | d | e | f | g | h | i | j |
|---|---|---|---|---|---|---|---|---|---|---|
| Set 1 sizes (bp) | 100 | 200 | 300 | 400 | 500 | 600 | 700 | 800 | 900 | 1000 |
| Set 2 sizes (bp) | 146 | 250 | 348 | 450 | 550 | 650 | 750 | 850 | 950 | 1050 |
| Set 3 sizes (bp) | 125 | 225 | 325 | 425 | 525 | 625 | 725 | 825 | 925 | 1025 |
| Set 4 sizes (bp) | 175 | 275 | 375 | 475 | 575 | 675 | 775 | 875 | 975 | 1075 |
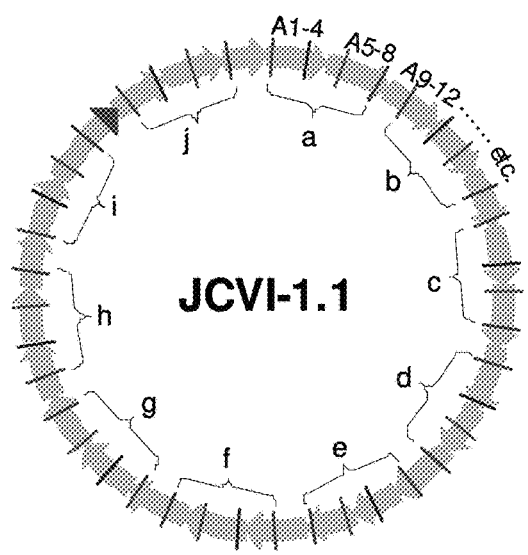
Figure 10 (A-B)

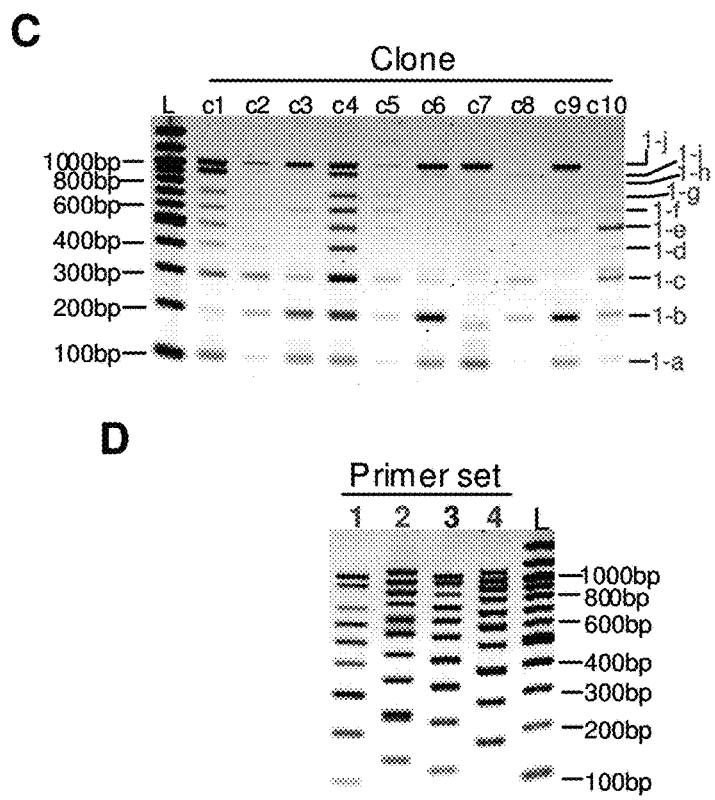
Figure 10 (C-D)
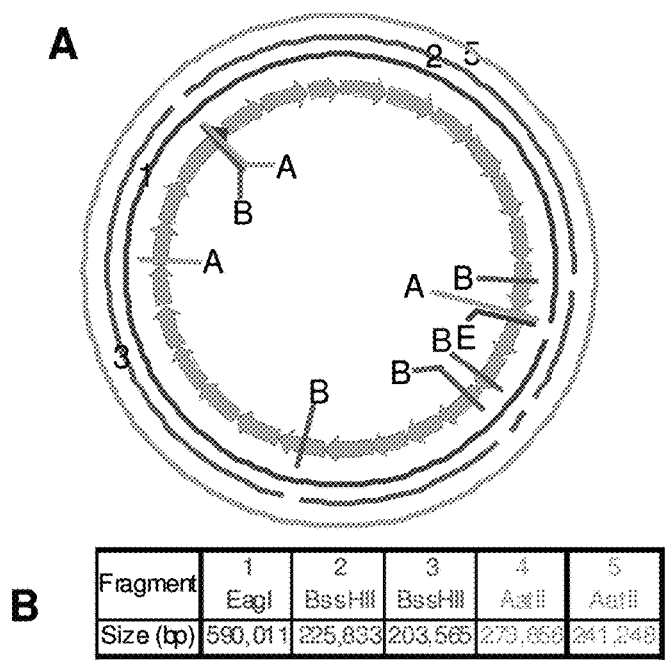
Figure 11 (A-B)

ASSEMBLY OF LARGE NUCLEIC ACIDS

CROSS-REFERENCE TO RELATED APPLICATIONS

This application claims benefit of U.S. provisional applications 60/978,388 filed 8 Oct. 2007; U.S. 60/983,549 filed 29 Oct. 2007; U.S. 61/062,214 filed 23 Jan. 2008; U.S. 61/023,392 filed 24 Jan. 2008, and U.S. 61/096,270 filed 11 Sep. 2008. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 616872000800Seqlist.txt | 30 Jun. 2009 | 4,096 bytes |

TECHNICAL FIELD

The invention relates to a method of assembling large nucleic acid molecules, by employing a combination of in vitro and in vivo assembly steps and to assembly of multiple overlapping nucleic acid fragments in yeast. In this aspect, the invention concerns accessing the ability of yeast to assemble long DNA molecules from a large number of components.

BACKGROUND ART

It has been possible to synthesize reasonably large nucleic acid molecules using automated step-wise synthesis. However, it appears that an upper limit for such methods to be practical is of the order of 5-30 kb. The longest synthetic DNA sequence known to the present inventors is that of a 32 kb polyketide synthase gene cluster reported by Kodumal, S. J., et al., *Proc. Natl. Acad. Sci. USA* (2004) 101:15573-15578. Many nucleic acid molecules of interest are considerably larger, including the smallest genome known of any cell that has been propagated in pure culture, *M. genitalium*, whose genome is approximately 600 kb. The only completely synthetic genomes so far reported are viral genomes, including the synthesis of poliovirus by Cello, J., et al., *Science*, (2003) 297:1016-1018; of φX174 bacteriophage assembled from synthetic oligonucleotides by Smith, H. O., et al., *Proc. Natl. Acad. Sci. USA* (2003) 100:15440-15445; and of HCV by Blight, K. J., et al., *Science* (2000) 290: 1972-1974.

It would be advantageous to synthesize larger DNA molecules. In one application, this can be done in order to provide the basis for determination of essential and non-essential genes. In another application, complete synthetic genomes that do not occur in nature can be constructed.

In the present invention, both in vitro and in vivo assembly methods are employed. In vitro assembly methods are described, for example, in PCT publication WO 2007/021944 based on PCT/US2006/031394 and in PCT publication WO 2007/032837 based on PCT/US2006/031214.

In vivo recombination in yeast is also known. Yeast recombination has since been applied to the construction of plasmids and yeast synthetic chromosome (YACs). In 1987 Ma, et al., constructed plasmids from two co-transformed DNA fragments containing homologous regions. In another process called linker-mediated assembly, any DNA sequence can be joined to a vector DNA in yeast using short synthetic linkers that bridge the ends (Raymond, C. K., et al., *Biotechniques* (1999) 26:134-138, 140-141; and Raymond, C. K., et al., *Genome Res.* (2002) 12:190-197). Similarly, four or five overlapping DNA pieces can be assembled and joined to vector DNA (Raymond, C. K., et al., *Biotechniques* (1999) 26:134-138, 140-141; and Ebersol, T., et al., *Nucleic Acids Res.* (2005) 33 e130), demonstrating that (i) yeast cells can take up multiple pieces of DNA and (ii) homologous yeast recombination is sufficiently efficient to correctly assemble the pieces into a single recombinant molecule.

Previous work has established that relatively large segments (>100 kb) of the human genome can be cloned in a circular yeast vector if the vector carries terminal 60 bp homologies ("hooks") that flank the human genome segment (Noskov, V. N., et al., *Nucleic Acids Res.* (2001) 29:E32). In addition, it is known that yeast will support at least 2 Mb of DNA in a linear centromeric yeast synthetic chromosome (YAC) described by Marschall, P., et al., *Gene Ther.* (1999) 6:1634-1637, and this has been used to clone sequences that are unstable in *E. coli* as described by Kouprina, N., et al., *EMBO Rep.* (2003) 4:257-262.

The ability of additional organisms to recombine nucleic acid fragments has also been explored. Holt, R. A., et al., *Bioessays* (2007) 29:580-590 have proposed using the lambda Red recombination system to assemble an 1830 kb *Haemophilus influenzae* genome within an *E. coli* cell. Itaya, M., et al., *Proc. Natl. Acad. Sci. USA* (2005) 102:15971-15976 and Yonemura, I., et al., *Gene* (2007) 391:171-177 have developed methods for assembling large DNA segments in *Bacillus subtilis*. These DNA molecules are built in the host organism only after stepwise addition of sub-fragments, by the addition of overlapping segments one at a time.

The assembly of an entire synthetic *M. genitalium* genome employing a combination of in vitro enzymatic recombination in early stages and in vivo yeast recombination in the final stage to produce the complete genome has been described by the present inventors in Gibson, D. G., et al., *Science* (2008) 319:1215-1220.

DISCLOSURE OF THE INVENTION

In one aspect, the invention relates to methods of assembling a large, optionally synthetic, nucleic acid molecule based on a nucleotide sequence of interest, or having any desired sequence. The methods are conveniently applicable to any sequence comprising about 50 kilobases or more.

Generally, a desired nucleic acid sequence is identified and used as a template for design of the building blocks for the desired nucleic acid sequence. The target molecule may comprise a sequence that occurs in nature, or may be designed by the practitioner. Cassettes representing overlapping segments of this sequence are designed to cover the entire desired sequence. In one preferred embodiment, some of the cassettes are designed to contain watermark sequences that allow for identification. The watermarks can be either non-coding or coding sequences. Typically the watermarks are located at sites known to tolerate transposon insertions so as to minimize biological effects on the final desired nucleic acid sequence. Once designed, the cassettes are synthesized using standard techniques such as synthesizing sequences de novo using individual nucleotides, or are obtained from the natural sources.

In one embodiment of the invention methods the cassettes, typically of the order of 2-10 kb are assembled in vitro, for example according to the techniques described in the above mentioned PCT publications, to obtain subsets of the desired nucleotide sequence. Several in vitro steps to assemble progressively larger portions of the desired sequence may be performed. In this manner, subsets that contain sequences on the order of 100 kb are obtained. These larger subsets of the desired sequence are then introduced into a host cell, where they are recombined and assembled. This step, too, is repeated if necessary until the desired large nucleic acid molecule is achieved.

The synthetic nucleic acid cassettes and subsets may be produced in the form of plasmids, megaplasmids, synthetic chromosomes such as plant synthetic chromosomes, bacterial synthetic chromosomes, mammalian synthetic chromosomes, yeast synthetic chromosomes, satellite synthetic chromosomes, sausage chromosomes, gigachromosomes, and megachromosomes. Prokaryotic and eucaryotic host cells are both contemplated for use with the disclosed methods, including but not limited to bacterial host cells like E. coli, yeast host cells, such as S. cerevisiae, and insect host cells, such as Spodoptera frugiperda.

Thus, in one aspect, the invention is directed to a method for the synthesis of a desired nucleic acid molecule, comprising:

a) providing a plurality of cassettes, each cassette containing the nucleotide sequence of a portion of the desired nucleic acid, wherein the cassettes contain overlapping portions of the nucleotide sequence of the desired nucleic acid molecule and wherein the cassettes, if combined according to the overlapping portions, provide the complete nucleotide sequence of the desired nucleic acid;

b) combining said cassettes in vitro to obtain a plurality of resulting subsets wherein said subsets contain overlapping portions of the desired sequence and wherein the subsets, if assembled according to the overlapping portions, would provide the nucleotide sequence of the desired nucleic acid; and c) assembling the subsets in vivo to obtain the desired nucleic acid molecule, wherein said assembly further includes an origin of replication.

As noted above, steps b) and/or c) may be repeated, depending on the size of the original cassettes and the length of the desired nucleic acid molecule. The assembly in step c) should include additional nucleic acid sequences that represent an origin of replication and may also include a centromere and/or a selectable marker. These may be present on a separate vector or vectors or may be included in one or more of the subsets employed in the in vivo recombination.

At least some of the cassettes may also contain a "watermark" which is foreign DNA that serves to identify the cassette in the assembled subsets or desired nucleic acid.

In another embodiment advantage is taken of the demonstration that yeast or other host cell is capable of assembling large numbers of fragments of nucleic acids with overlapping sequences, so that very large nucleic acid molecules may be assembled from multiple cassettes in vivo. Accordingly, in another aspect, the invention is directed to a method to assemble, simultaneously, at least 10 nucleic acid fragments having overlapping sequences in a host cell which method comprises transforming a culture of said cells with a mixture of said fragments wherein DNA encoding an origin of replication and preferably a centromere is included among said fragments, and culturing said host or an alternative replication cell to which the assembled fragments are transferred.

In one embodiment, a selectable marker is further included among the fragments.

In one variation of this embodiment, two of said fragments contain at one of their termini a telomeric sequence for protection against exonuclease activity. In still another variation of this embodiment, an origin of replication operable in a different host is included among said fragments. These variations may also be applied to the in vivo step(s) of the method that employs an in vitro/in vivo combination of steps described above.

In the in vivo recombination aspect, the fragments can either be double-stranded or single-stranded. The double-stranded fragments are generally 100-5×10$^6$ base pairs and the single-stranded fragments are generally shorter, but can range from 40-1,000 nucleotides. The wide range of sizes of the fragments is intended to include all intermediate integral values. Of course, it is not necessary for all of the fragments to be the same size, or even to be of the same order of magnitude in size.

Thus, in this aspect, the invention is directed to a method to assemble 10 or more DNA fragments into a target DNA molecule, which method comprises:

(a) transfecting a culture of host cells with a mixture containing a sufficient number of copies of each of said at least 10 fragments to result in uptake of copies amounting to at least about double the number of different fragments by the average cell in said culture, wherein said fragments contain overlapping sequences of at least 10 base pairs and wherein the overlapping sequences are arranged so that the sequences overlap to provide a desired order of assembly and wherein an origin of replication is included among said fragments;

(b) permitting sufficient time for assembly of said fragments in said host culture; and (c) either
(i) culturing said host to obtain sufficient copies of the assembled nucleic acid molecule for recovery or
(ii) extracting DNA from said host and transfecting an alternative culture allowing said alternative culture to replicate sufficient copies of said assembled nucleic acid molecule for recovery.

If option (i) is employed, the origin of replication will be an origin of replication operable in the host cells. If option (ii) is performed, the origin of replication must be compatible with the alternative culture. If option (i) is performed, inclusion of a centromere is optional because a consequence of lacking it is simply that the replicated DNA would accumulate in a single cell rather than being distributed to daughter cells. It may not be absolutely necessary to assure distribution of the replicated DNA molecules into daughter cells. In addition, a selectable marker may be included.

The DNA encoding the origin of replication (and/or the two optional elements—the centromere and selectable marker) may be supplied as a separate fragment or as a portion of one or more of the fragments to be assembled. Further, as explained below, a DNA sequence operable as an origin of replication may be found indigenously in the fragments intended to be assembled and need not necessarily be otherwise supplied.

The DNA molecule may be assembled into a circular assembly thus preserving it from exonuclease activity, or two of the assembled fragments may comprise telomeres at one terminus of each so that a linear assembly bracketed by telomeres is obtained.

In some embodiments, a selectable marker is included in the fragments and culturing is done under selection conditions and the method of the invention may further include recovering the assembled DNA from either the original culture or the alternative culture. The assembled fragments may be recovered from the culture or from colonies grown from individual cells. According to the method of the invention, although at least one target DNA molecule must be assembled from 10 or more fragments, multiple assemblies of DNA molecules can be effected simultaneously in the same cell.

All of the features just described also apply to the final in vivo steps in the combination in vitro/in vivo synthesis above.

In other aspects, the invention is directed to synthetic large nucleic acid molecules synthesized by the method of the invention and which do not occur in nature. In general, because the in vivo recombination steps require the inclusion at least of an origin of replication operable in a host cell, the resultants of the method will be novel. The invention is also directed to cultures of cells which contain the synthetic large nucleic acid molecules synthesized by the invention method and methods to use such cultures.

BRIEF DESCRIPTION OF THE DRAWINGS

FIG. 3 shows strategy for the five-stage assembly of the *M. genitalium* chromosome.

FIGS. 4A-4C show assembly of cassettes by in vitro recombination.

FIG. 9 is a diagram of construction of a synthetic *M. genitalium* genome in yeast.

FIGS. 10A-10D show multiplex PCR analysis to screen for yeast cells transfected with 25 segments of DNA.

MODES OF CARRYING OUT THE INVENTION

Figure 1:
FIG. 1 shows a plot of probability that a whole set of 25 DNA pieces is taken up (success) versus number of DNA pieces taken up by an individual cell according to a computer simulation.

The method of the invention is suitable for facile construction of nucleic acid molecules that sufficiently large that simple in vitro construction is not feasible. Currently, in vitro assembly of nucleic acid molecules larger than about 300 kb is problematic. Larger pieces can be assembled, however, by recombination in a suitable host cell capable both of recombining sequences with overlapping ends and tolerating large DNA molecules of 2-10 Mb or more.

Thus, one application of the invention relates to the construction of a synthetic genome or genome fragment based on the genetic information obtained from an organism. Genetic information derived from whole genomes can be used as basis for designing the synthetic sequences of interest. For example, the nucleic acid sequence of a whole mammalian chromosome or a fragment thereof can be the template for an artificially generated construct. Genomic sequences from a number of organisms are publicly available and can be used with the disclosed methods. These genomic sequences include but are not limited to information obtained from *Aeropyrum pernix; Agrobacterium tumefaciens; Anabaena; Anopheles gambiae; Apis mellifera; Aquifex aeolicus; Arabidopsis thaliana; Archaeoglobus fulgidus; Ashbya gossypii; Bacillus anthracis; Bacillus cereus; Bacillus halodurans; Bacillus licheniformis; Bacillus subtilis; Bacteroides fragilis; Bacteroides thetaiotaomicron; Bartonella henselae; Bartonella quintana; Bdellovibrio bacteriovorus; Bifidobacterium longum; Blochmannia floridanus; Bordetella bronchiseptica; Bordetella parapertussis; Bordetella pertussis; Borrelia burgdorferi; Bradyrhizobium japonicum; Brucella melitensis; Brucella suis; Buchnera aphidicola; Burkholderia mallei; Burkholderia pseudomallei; Caenorhabditis briggsae; Caenorhabditis elegans; Campylobacter jejuni; Candida glabrata; Canis familiaris; Caulobacter crescentus; Chlamydia muridarum; Chlamydia trachomatis; Chlamydophila caviae; Chlamydophila pneumoniae; Chlorobium tepidum; Chromobacterium violaceum; Ciona intestinalis; Clostridium acetobutylicum; Clostridium perfringens; Clostridium tetani; Corynebacterium diphtheriae; Corynebacterium efficiens; Coxiella burnetii; Cryptosporidium hominis; Cryptosporidium parvum; Cyanidioschyzon merolae; Debaryomyces hansenii; Deinococcus radiodurans; Desulfotalea psychrophila; Desulfovibrio vulgaris; Drosophila melanogaster; Encephalitozoon cuniculi; Enterococcus faecalis; Erwinia carotovora; Escherichia coli; Fusobacterium nucleatum; Gallus gallus; Geobacter sulfurreducens; Gloeobacter violaceus; Guillardia theta; Haemophilus ducreyi; Haemophilus influenzae; Halobacterium; Helicobacter hepaticus; Helicobacter pylori; Homo sapiens; Kluyveromyces waltii; Lactobacillus johnsonii; Lactobacillus plantarum; Legionella pneumophila; Leifsonia xyli; Lactococcus lactis; Leptospira interrogans; Listeria innocua; Listeria monocytogenes; Magnaporthe grisea; Mannheimia succiniciproducens; Mesoplasma florum; Mesorhizobium loti; Methanobacterium thermoautotrophicum; Methanococcoides burtonii; Methanococcus jannaschii; Methanococcus maripaludis; Methanogenium frigidum; Methanopyrus kandleri; Methanosarcina acetivorans; Methanosarcina mazei; Methylococcus capsulatus; Mus musculus; Mycobacterium bovis; Mycobacterium leprae; Mycobacterium paratuberculosis; Mycobacterium tuberculosis; Mycoplasma gallisepticum; Mycoplasma genitalium; Mycoplasma mycoides; Mycoplasma penetrans; Mycoplasma pneumoniae; Mycoplasma pulmonis; Mycoplasma mobile; Nanoarchaeum equitans; Neisseria meningitidis; Neurospora crassa; Nitrosomonas europaea; Nocardia farcinica; Oceanobacillus iheyensis*; Onions yellows phytoplasma; *Oryza sativa; Pan troglodytes; Pasteurella multocida; Phanerochaete chrysosporium; Photorhabdus luminescens; Picrophilus torridus;*

*Plasmodium falciparum; Plasmodium yoelii yoelii; Populus trichocarpa; Porphyromonas gingivalis Prochlorococcus marinus; Propionibacterium acnes; Protochlamydia amoebophila; Pseudomonas aeruginosa; Pseudomonas putida; Pseudomonas syringae; Pyrobaculum aerophilum; Pyrococcus abyssi; Pyrococcus furiosus; Pyrococcus horikoshii; Pyrolobus fumarii; Ralstonia solanacearum; Rattus norvegicus; Rhodopirellula baltica; Rhodopseudomonas palustris; Rickettsia conorii; Rickettsia typhi; Rickettsia prowazekii; Rickettsia sibirica; Saccharomyces cerevisiae; Saccharopolyspora erythraea; Salmonella enterica; Salmonella typhimurium; Schizosaccharomyces pombe; Shewanella oneidensis; Shigella flexneria; Sinorhizobium meliloti; Staphylococcus aureus; Staphylococcus epidermidis; Streptococcus agalactiae; Streptococcus mutans; Streptococcus pneumoniae; Streptococcus pyogenes; Streptococcus thermophilus; Streptomyces avermitilis; Streptomyces coelicolor; Sulfolobus solfataricus; Sulfolobus tokodaii; Synechococcus; Synechocystis; Takifugu rubripes; Tetraodon nigroviridis; Thalassiosira pseudonana; Thermoanaerobacter tengcongensis; Thermoplasma acidophilum; Thermoplasma volcanium; Thermosynechococcus elongatus; Thermotagoa maritima; Thermus thermophilus; Treponema denticola; Treponema pallidum; Tropheryma whipplei; Ureaplasma urealyticum; Vibrio cholerae; Vibrio parahaemolyticus; Vibrio vulnificus; Wigglesworthia glossinidia; Wolbachia pipientis; Wolinella succinogenes; Xanthomonas axonopodis; Xanthomonas campestris; Xylella fastidiosa; Yarrowia lipolytica; Yersinia pseudotuberculosis;* and *Yersinia pestis.*

Additionally, the presently described methods are equally applicable to presently unpublished nucleotide sequences, as they become available, including those that characterize multicellular organisms such as higher plants, such as corn and rice, mammals such as mice, pigs, cows, and companion animals. Many of these are available at the present time.

It is apparent, from a review of the examples below and of the discussion of the methods of the invention, that its applicability is not limited to constructing synthetic genomes that mimic those that are present in nature. The initial cassettes useful in constructing larger DNA molecules can be chosen in any manner desired by the practitioner. Thus, portions of genomes of various organisms can be included in the same DNA molecule or arbitrary designs of the cassettes can be employed. The original cassettes can be either synthesized or isolated from naturally occurring DNA or by reverse transcription of RNA.

It may also be desirable simply to assemble members of an individual metabolic pathway or to assemble multiplicities of metabolic pathways according to this method. Metabolic pathways which do not exist in nature can be constructed in this manner. Thus, enzymes which are present in one organism that operate on a desired substrate produced by a different organism lacking such a downstream enzyme, can be encoded in the same organism by virtue of constructing the assembly encoding both enzymes. Multiple enzymes can thus be included to construct complex metabolic pathways. In addition, combinatorial libraries can be prepared by mixing fragments where one or more of the fragments is supplied with the same overlapping sequences, but different intervening sequences encoding enzymes or other proteins.

Genetic pathways can be constructed in a combinatorial fashion such that each member in the combinatorial library has a different combination of gene variants. For example, a combinatorial library of $6^5$ variants can be constructed from 30 individual DNA elements where 5 fragments are assembled and wherein each of the 5 fragments has 6 variants.

In one embodiment, the method of the invention employs two stages of synthesis. In the first stage, relatively small nucleic acid molecules are assembled in in vitro ligation reactions. In the methods described in the PCT publications set forth above, double-stranded DNA is used; however, these and other methods may be used for assembling single-stranded DNA. For single stranded or double-stranded DNA, in addition to these methods, an isothermal method can also be employed. In one form, an efficient reaction composition that is operable on double stranded nucleic acid is used. It employs three enzymes—a T5 exonuclease, a processive polymerase and a Taq ligase. The details of this system are as follows: The reaction mixture includes T-5 exonuclease, a PHUSION® (Thermo Fisher Scientific Oy LLP, Vantaa, FI) polymerase, Taq DNA ligase, an appropriate buffer such as ISO buffer (Tris pH 7.5, $MgCl_2$, dNTP's, NAD, DTT, PEG 8,000) and assembly occurs under isothermal conditions in an hour or less. This reaction mixture can be frozen and used directly by adding it to the oligomeric fragments, including double stranded forms thereof and incubating at 50° C. for 10-60 minutes. The method using this composition employs double-stranded nucleic acids since the T-5 exonuclease chews back one strand of the double-strand to expose overlapping sequences. The PHUSION® (Thermo Fisher Scientific Oy LLP, Vantaa, FI) polymerase and DNA ligase then effect repair after annealing of the overlapping strands. Typical concentrations of the components of the ISO buffer are 100 mM Tris-Cl 5% PEG 8,000, 10 mM $MgCl_2$, 10 mM DTT, 1 mM NAD, and 200 µM dNTP's.

In the second phase, when larger subsets of the desired sequence have been obtained, in vivo recombination techniques are employed. While in some instances, in particular where the subsets are relatively small, prokaryotic cells may be used. However, for ligation of larger subsets, eukaryotic systems, and, in particular, yeast is preferred. The features of in vivo recombination are discussed in detail with respect to the alternative embodiment employing complete in vivo assembly described below.

The in vivo assembly of multiple DNA fragments, in general, 10 or more DNA fragments, is exemplified below using yeast as a host culture. However, other hosts could be substituted for yeast, such as *Deinococcus Radiodurans*. Other organisms are known which can facilitate recombination.

In addition, it may be advantageous to mutate or delete genes that are known to perform non-homologous enjoining. In *S. cerevisiae*, these genes include Ku and DNA ligase IV as well as Rad 50, Mrell and Xrs2. This would minimize background unwanted recombination.

Thus, the demonstration of assembly of multiple fragments in yeast is for illustration only. As defined herein, a "close" culture is a culture into which the fragments are transfected for assembly. And "alternate" culture refers to an alternative type of organism or cell culture to which the assembled DNA may be transferred for further replication.

The use of in vivo recombination as illustrated in yeast offers a powerful tool for assembling multiple DNA fragments in a single efficient assembly step, and thus, in an alternative embodiment, the prior performance of in vitro subset assembly is not employed. This embodiment takes advantage of the capabilities of yeast or another host to absorb and recombine multiple fragments and to tolerate and propagate large assemblies that result from this recombination. In vivo assembly is appropriate for assembling as many as 10-500 fragments. Illustrated below, assembly of 25 fragments has been successfully demonstrated. The basic technique described is able to assemble 50, 75, 100, 200, 300, 400 or 500 such fragments. The fragments to be assembled may be double-stranded and comprise $100-5\times10^6$ base pairs or any intermediate number, including 200, 500, 1,000, 5,000, 10,000, 100,000 or $10^6$ base pairs or may be single-stranded and contain 40-1,000 nucleotides or any intermediate integer such as 100 or 500 nucleotides. The number desired to be assembled may depend on the size of the fragments themselves. As noted above, not all of the fragments need to be the same size or even the same order of magnitude. Thus, the fragments in a single mixture may vary across the range. Very large assemblies can be tolerated.

A construct of any size can be assembled inside a yeast cell so long as the sub-fragments can get into the nucleus, and the constructed DNA segment is completely and accurately replicated and not toxic to the host cell.

DNA replication of the assembled molecule in yeast is dependent on the presence of a highly conserved and essential A-element or autonomously replicating sequence (ARS) consensus sequence (5'-$^T_A$TTTA$^T_C$$^A_G$TTT$^T_A$-3')(SEQ ID NO:1)(reviewed in Bell, S. P., *Curr. Opin. Genet. Dev.* (1995) 6:1634-1637). Statistically this sequence should be present once every ~262 kb in an assembled construct when all 4 bases are equally represented. As noted above, these origins of replication may automatically be present in the pieces whose assembly is desired, making the deliberate supply of a particular origin of replication unnecessary. In the illustration of Example 4 below, these elements should be present more frequently in fragments representing the *M. genitalium* genome (26.9 times on average, or once every ~16 kb) of the genome itself given its high A+T composition. This has been confirmed as there are 20 instances of the ARS consensus sequence in the assembled genome including 2 from the vector. This is an important consideration since it has been shown that a 170 kb YAC lacking efficient origins of replication can invoke a cell-cycle checkpoint response in yeast (van Brabant, A. J., et al., *Mol. Cell.* (2001) 7:705-713).

Thus, assemblies of as much as 5 Mb up to 20 Mb could be assembled in yeast, and the in vivo aspects of the methods of the invention offer the opportunity to assemble 6-1,000 or an intermediate number of independent DNA fragments using the method of the invention to assemble sequences as long as 20 Mb.

Regardless of the host, for the assembly to occur, the fragments to be assembled must contain sequences that are overlapping at their termini. In one embodiment, the overlaps are approximately 10 bp; in other embodiments, the overlaps may be 15, 25, 50, 60 or 80 bp and all integers within this range. Not all of the overlap lengths of all of the fragments need be the same. However, in order to avoid misassembly, individual overlaps that should not be duplicated among the fragments.

In the in vivo method of the assembly, a mixture of all of the fragments to be assembled is used to transfect the host recombination and assembly cell using standard transfection techniques. The ratio of the number of molecules of fragments in the mixture to the number of cells in the culture to be transfected must be high enough to permit at least some of the cells to take up more molecules of fragments than there are different fragments in the mixture. This is illustrated in the Example below, where for a mixture containing 25 different fragments, it is estimated that sufficient molecules of fragments are present in the mixture that the average cell would take up at least 40 pieces; in this illustration, approximately 1 in 1,000 cells will contain each of the 25 different fragments. By enhancing the level of uptake, however, so that the average cell would take up at least 100 pieces, a much higher percentage of the cells will contain all 25 different pieces. The larger the number taken up by the average cell, the greater the probability that one representative of each different fragment will be included in the uptake.

Thus, for assembly of 10 fragments, it is desirable that the mixture contain a sufficient number of molecules of fragments to provide the average cell with 15-20 pieces; similarly, if there are 100 different fragments, in one embodiment, the mixture is supplied at sufficient concentration that the average cell would take up 150-200 fragments.

In order to provide a workable method, included in the fragments to be assembled must be DNA providing an origin of replication, optionally and preferably a centromere, and optionally and preferably a selectable marker. The origin of replication may be operable only in the initial, or in an alternate type of cell intended to carry out replication, or shuttle vectors may be used permitting for example both replication in the initial host and subsequent transfection of assembled sequences in an alternative host, such as *E. coli* or *Bacillus*. It is convenient, but not necessary, to include all two or three of these elements in a single one of the fragments. In the presence of these elements only cells with successfully assembled sequences will be recovered. Because linear DNA unprotected by telomeres is subject to degradation, only assembled circular DNA or telomere-protected assembled DNA will survive to replicate.

The origin of replication may be one selected by the practitioner and included in one of the fragments whose assembly is desired or may be included on a separate vector fragment included in the assembly. However, depending on the nature of the fragments, a supplemental origin of replication may not be required due to the coincidental presence of sequences that are operable as origins of replications indigenous to the fragments themselves. There is actually a rather high probability that such sequences will indeed occur.

The presence of a centromere merely assures that replicated DNA will be distributed between the mother and daughter cells during replication. In some embodiments, multiple copies of the assembled DNA may be permitted to remain in the same cell and still be recovered effectively. Thus, although the presence of a centromere is preferable, it is not completely necessary. Similarly, the presence of a selectable marker is optional but facilitates recovery of successful transformants in those cells where the DNA has been assembled into a circular pattern, or is telomere-protected.

In some embodiments, a circular DNA is formed as noted above. However, in other embodiments, two of the fragments may be supplied with telomeres such that assembly of a linear molecule protected from degradation results, in imitation of the yeast genome itself. Again, the selectable marker facilitates identification of successful colonies.

In some embodiments, rather than forming only a single target DNA molecule from fragments in a single host cell, multiple assemblies of fragments may be obtained. Thus, for example, two separate products, one assembled from 10 fragments and the other assembled from 5, or one assembled from 20 fragments and the other assembled from 50, may be formed in a single host cell.

In one embodiment, cells with successfully assembled circular or telomere-protected DNA sequences are propagated in the host and isolated from the host culture or from cultures obtained from individual host cell colonies. In an alternative embodiment, the host culture is treated with the mixture of fragments for a short period, about 15 minutes-2 hours, and then total DNA is extracted and transfected into an alternative cell type, such as E. coli or Bacillus. In this embodiment, a vector containing a suitable origin of replication for the alternative cell type will be used. This embodiment in some cases has the advantage of shortening the time required to recover sufficient quantities of the assembled DNA due to the shorter multiplication time of these alternative cells. For example, whereas 2-3 days is required to obtain sufficient molecules of assembly for analysis in yeast, the replication time of E. coli will permit such recovery within several hours.

Only a small percentage of the cells contained in the treated culture need take up sufficient numbers of fragments and recombine them in order to provide successful reassembly. Those cells which fail will not be represented in the culture because the DNA in cells where assembly has not occurred will not replicate. If desired, as mentioned above, in some embodiments, a selectable marker may also be included which provides an additional, perhaps redundant, method to limit the cells from which DNA is extracted to those having the desired construct.

The assembly of multiple fragments of DNA into a single circular or telomere-bracketed molecule may be used for the construction of any desired assembly. A naturally occurring genome, such as M. genitalium illustrated below, can be assembled in this manner and thus prepared synthetically.

Alternative genomes, such as those of E. coli or other genomes such as H. influenzae could be assembled in this manner. While it would be possible simply to isolate the genome and replicate it in the initial host, because of the capability of the host to assemble multiple fragments, the genome need not be extracted intact from the organism. Disassembled forms automatically would contain the overlapping sequences required for reassembly.

Upon assembly of sufficient DNA molecules, these may be recovered from the host or alternative host cell culture. Standard isolation techniques are employed and these are well known in the art. By "isolated" is meant that the DNA is present outside of its natural environment. Thus, even the reassembled DNA contained in the cultures in which it has been caused to reassemble can be considered "isolated" in this sense. Recovery of the DNA from these cells, however, may be desirable in order to further manipulate the assembled DNA or to culture it in other cells, including mammalian, plant or insect cells.

The determination of the concentration of fragments necessary to transfect a host cell culture such as yeast is determined empirically as noted above. A multiplicity of cells is required to assure that a sufficient number will take up the appropriate number of fragments, and sufficient fragments must be supplied to effect this uptake. An illustrative determination with respect to the assembly of 25 fragments as has been accomplished in Example 4 hereinbelow, is illustrated as follows:

In this illustration, an individual host cell must take up at least one each of the 25 DNA pieces in order to assemble a complete assembly of 25 fragments. If a cell randomly takes up exactly 25 pieces, the probability that it takes up one of each is $25!/25^{25}=1.7\times10^{-10}$, a very rare occurrence. It is thus desirable that the average host cell take up substantially more than 25 pieces. If a host cell randomly takes up N>25 equally represented pieces, what is the probability of getting all 25 different pieces? A solution for this version of the "collector's problem" is difficult to calculate across the entire range of probabilities (Feller, W., An Introduction to Probability Theory and Its Applications (1950) Wiley, New York); however, an approximate answer is readily obtained by computer simulation, as shown in FIG. 1, where the Y-axis represents probability of success and the X-axis represents the number of copies taken up by a host cell. To obtain this plot, N draws were made from a bag of 25 objects (pieces of DNA), replacing the object after each draw. The trial was a success if all 25 objects were drawn at least once. A million trials were made for each N to obtain a good approximation to the true probability of success. FIG. 1 shows that if a cell takes up ~90 pieces, it has about a 50% chance of taking up all 25 different pieces. If $10^8$ host cells are exposed to DNA, even if the average cell takes up only 40 pieces, about 1 in 1,000 would get a complete set of pieces.

The efficiency of DNA uptake and assembly in yeast and other assembly hosts is not known. If recombination is highly efficient, then only a few cells in the population might need to take up a complete set of overlapping pieces. If the efficiency is low, then relatively more cells would need a complete set.

Any arbitrary large DNA molecule can be assembled using the methods of the invention. One particularly useful application is the assembly of genomes from microorganisms. In one application, the sequence to be assembled can comprise the nucleotide sequence of an organism's entire genome or a fraction thereof. Nucleotide sequences to be assembled by the disclosed method can be obtained from any organism, whether Protista, Archaebacteria, Eubacteria, Fungi, Platae, or Animalia. Sequence information from viral genomes is also contemplated for use with the disclosed methods.

As used in regard to either the combination in vitro/in vivo synthesis method or the total in vivo recombination synthesis method, "cassette" refers to a starting nucleic acid molecule that contains a portion of the sequence of the desired target nucleic acid molecule that has been synthesized from single nucleotides or which has been obtained from the genome of an organism itself by fractionation or restriction digested genomic DNA or which has been obtained from cDNA reverse transcribed from mRNA in an organism. The initial cassettes are typically on the order of 2-10 kb and all intermediate values and are preferably on the order of approximately 5 kb. These cassettes may also be assembled by ligating smaller oligonucleotides. Typically, the cassettes are double-stranded, although single-stranded cassettes could be used as well. The term "cassettes" also includes additional combinations of starting cassettes which are obtained from in vitro methods of ligation. The cassettes obtainable by in vitro ligation of initial portions of the desired sequence typically range from about 15 kb to about 200 kb and all integral values in between. These assemblies can either be called "cassettes" or "subsets" where "subsets" refers to a subset of the sequence of the desired target nucleic acid molecule; this refers to the fragments used for in vivo recombination in the in vitro/in vivo method.

"Subset" means an assembly of cassettes that is of appropriate size for in vivo recombination in the in vitro/in vivo method. These can also be single or double stranded. Depending on the size of the target nucleic acid molecule, such subsets are typically in the range of 50-500 kb and integral values between these extremes. Thus, this embodiment of the methods of the invention begins with initial cassettes and, through assembly thereof, results in "subsets" which are then assembled in vivo. It is convenient, but not required, to assemble cassettes in vitro to a size of approximately 75-200 kb and then to conduct further assembly of subsets of this size in vivo.

As described below in Examples 1-3, the entire *M. genitalium* JCVI-1.0 chromosome, was prepared based on *M. genitalium* G37, and propagated in yeast using a TAR-BAC cloning vector. This construct is more than an order of magnitude larger than previously reported synthetic DNA products. This chromosome may be installed into a receptive *Mycoplasma* cytoplasm to produce a living "synthetic" cell (Lartigue, C., et al., *Science* (2007) 317:632-638). The synthetic chromosome contains five short watermark sequences at intergenic locations that tolerate transposon insertions, and these insertions are not expected to affect viability. There is also an insertion in gene MG408 for the purpose of eliminating pathogenicity, and the synthetic genome carries an aminoglycoside resistance gene that can be used for selection in transplantation experiments. As this exact insertion is present in a viable *M. genitalium* strain, it is not expected to affect viability.

The efficiency of in vitro procedures declines as the assemblies become larger. This may be due to formation of concatamers, which may form preferentially over the circular form during the reactions. In addition, large bacterial synthetic chromosomes (BAC's) (>100 kb) transform less efficiently. Sheng, et al., found that a 240 kb BAC transformed 30 times less efficiently than an 80 kb BAC in the same recipient strain of *E. coli* (Sheng, Y., et al., *Nucleic Acids Res.* (1995) 23:1990-1996.

In Examples 2 and 4 below, in vivo yeast recombination was used. In Example 2, the overlapping pieces, each of which has terminal 80 bp homologies to adjacent pieces were efficiently assembled and then joined to overlapping vector DNA by the transformation associated recombination (TAR) mechanism in yeast. Two quarters of the *M. genitalium* genome could be efficiently cloned as half genomes in a yeast vector, and more surprisingly, 4 quarters were recombined and cloned as whole genomes.

Construction of the synthetic chromosome and successful transplantation into a *Mycoplasma* species is a first step in efforts to make a minimal cell using the synthetic genomics approach. The cassette-based assembly strategy facilitates construction of a minimal cell. Putatively dispensable genes can be deleted from individual cassettes. A mixture of native and deleted cassettes can then be assembled. This approach would create a library with individual members ranging from completely native to extensively deleted genomes. Transplantation of the genome library into a recipient *Mycoplasma* would generate many new viable variants. Gel electrophoresis of the transplanted genomic DNA could then be used to select the smallest genome for study as a reduced or possibly minimal genome.

The *M. genitalium* JCVI-1.0 is a small genome with a peculiar use of the termination codon, UGA, for tryptophan. This may make cloning in *E. coli* and other organisms less toxic because most of the *M. genitalium* proteins will be truncated. If other constructions use this code, transplantation to generate a synthetic cell would need to be carried out in a cytoplasm that can properly translate the UGA to tryptophan. It might be possible to use other codon changes as long as there is a receptive cytoplasm with appropriate codon usage.

In the examples set forth below, the objective was to produce a cloned synthetic genome 582,970 base pairs in length with exactly the sequence that was designed. This is not trivial because differences (errors) between the actual and designed sequence can arise in several ways, including an error in the sequence used to prepare the cassettes, in the cassette produced or occurring during repair of assembly junctions. Propagation of assemblies in *E. coli* or yeast could also lead to errors. In the latter two instances, errors could occur at a late stage of the assembly. Therefore, it is prudent to sequence genome assembly clones at various points during assembly. In the example below, every type of error described above was found, but the number of errors was small and they were successfully corrected.

For example, during sequence verification of the C50-77 ¼ molecule described below two single base pair deletions were detected. One was traced back to a synthesis error in cassette 54. An error in cassette 68 occurred because an incorrect sequence was transmitted to the synthesizer of this cassette. The error in cassette 54 was corrected by the synthesizer. Cassette 68 was corrected by replacing a restriction fragment containing the error with a newly synthesized fragment. C50-77 was reassembled and sequenced. The two errors were corrected, but two new single base substitution errors appeared. Taq polymerase misincorporation in a joint region likely caused one of these errors. The other remains unexplained, but could have arisen during propagation in *E. coli*. One final reassembly yielded the correct sequence for C50-77 that was used to assemble the whole chromosome.

Preparation A

Confirmation of the Sequence of the *M. genitalium* Genome

The *M. genitalium* G37 genome was originally sequenced in 1995. However, the genome was isolated and re-sequenced because an error in sequence could result in a non-viable synthetic genome. The sequence determined differed at 34 sites from the original sequence. See Glass, J. I., et al., *PNAS (USA)* (2006) 103:425-430. The revised sequence specifies exactly the genome of viable *M. genitalium* G37.

The following examples are offered to illustrate but not to limit the invention, and describe in detail the synthesis of the complete genome of *M. genitalium*. In the combination in vitro/in vivo synthesis, provided in Examples 1-3, an overview of the synthesis may be summarized as follows:

This synthetic 582,970 bp *Mycoplasma genitalium* JCVI 1.0 genome contains all the genes of wild type *M. genitalium* G37 except MG408, which is disrupted to block pathogenicity. The genome also contains added "watermark" sequences located at intergenic sites known to tolerate transposon insertions, for identification of the genome as synthetic. Antibiotic resistance markers are included to allow its selection. Overlapping "cassettes" of 5-7 kb, assembled from chemically synthesized oligonucleotides, were joined in vitro to produce intermediate assemblies of ~24 kb, ~72 kb ("⅛ genome"), and ~144 kb ("¼ genome"), which were all cloned as bacterial synthetic chromosomes (BAC) in *Escherichia coli*. Most of these intermediate clones were sequenced and clones of all four ¼ genomes with the correct sequence were identified. The complete synthetic genome was assembled by transformation associated recombination (TAR) cloning in the yeast *Saccharomyces cerevisiae*, then isolated and sequenced. A clone with the correct sequence was identified. This synthetic *M. genitalium* genome can also be isolated.

Figure 2:
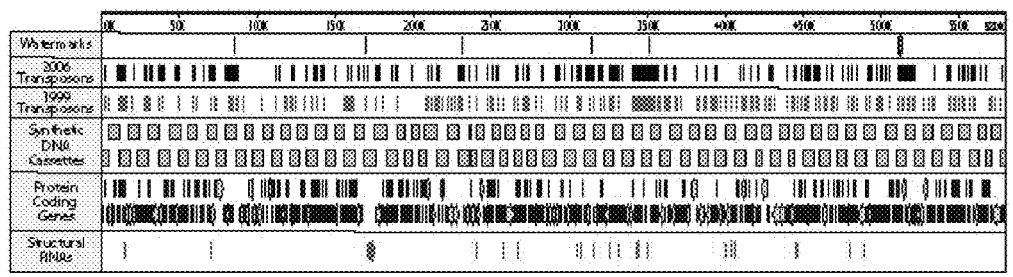
FIG. 2 is a diagram of the 582,970 bp *M. genitalium* JCVI-1.0 synthetic genome.

FIG. 2 shows the synthetic genome. Features shown include: watermarks and the aminoglycoside resistance marker, locations of the viable Tn4001 transposon insertions, locations of the overlapping synthetic DNA cassettes that comprise the whole genome sequence, locations of the 485 *M. genitalium* protein coding genes, and locations of the 43 *M. genitalium* rRNA, tRNA and structural RNA genes.

FIG. 3 diagrams the overall plan. In the first stage of assembly 4 cassettes were joined to make an A-series assembly approximately 24 kb in length. In the next stage, 3 A-assemblies went together to make a total of eight approximately 72 kb B-series assemblies. The ⅛ genome, B-assemblies were taken 2 at a time to make ¼ genome, C-series assemblies. These assemblies were all made by in vitro recombination and cloned into *E. coli* using BAC vectors. Half genome and full genome assemblies were made by in vivo yeast recombination. Assemblies in bold boxes were sequenced to validate their correctness.

In the first stage, sets of 4 neighboring cassettes were assembled by in vitro recombination as described below and joined to a BAC vector DNA to form circularized recombinant plasmids with ~24 kb inserts. For example, cassettes 1 to 4 were joined together to form the A1-4 assembly, cassettes 5 to 8 were assembled to form A5-8, and so forth. Cassettes 40 and 41 were merged to form a single cassette labeled 41*, hence the 101 original cassettes were reduced to 100, yielding 25 A-series assemblies. In the second stage, the 25 A-series assemblies were taken 3 at a time to form B-series assemblies. For example, B1-12 was constructed from A1-4, A5-8, and A9-12. The one exception was B62-77, which was made from 5 A-assemblies. This reduced the 25 A-assemblies to only 8 B-assemblies, each about ⅛ of a genome in size (~72 kb). In the third stage, the ⅛-genome B-assemblies were taken 2 at a time to make four C-assemblies, each approximately ¼-genome (~144 kb) in size. These first three stages of assembly were done by in vitro recombination and cloned into *E. coli*.

EXAMPLE 1

In Vitro Assembly of a Partial *M. genitalium* Genome

The native 580,076 kb *M. genitalium* genome sequence (*Mycoplasma genitalium* G37 ATCC 33530 genomic sequence; accession No. L43967 (Glass, J. I., et al. *PNAS (USA)* (2006) 103:425-430) was partitioned into 101 cassettes of approximately 5 to 7 kb in length that were individually synthesized and sequenced. In general, cassette boundaries were placed between genes so that each cassette contained one or several complete genes to simplify the future deletion or manipulation of the genes in individual cassettes. Most cassettes overlapped their adjacent neighbors by 80 bp; however, some segments overlapped by as much as 360 bp. Cassette 101 overlapped cassette 1, thus completing the circle.

Short "watermark" sequences were inserted in cassettes 14, 29, 39, 55 and 61 at intergenic sites known to tolerate transposon insertions to allow differentiation of the synthesized genome from the native genome. In addition, a 2,520 bp insertion in gene MG408 (msrA), which includes an aminoglycoside resistance gene, was placed in cassette 89. It has been shown that a strain with this specific defect in this virulence factor cannot adhere to mammalian cells, thus eliminating pathogenicity in the best available model systems. This cassette was synthesized by GENEART (Regensburg, Germany). The synthetic genome with all of the above insertions is 582,970 bp.

Cassettes 1 to 31, 36 to 39, 52 to 88 and 90 to 101 were synthesized by Blue Heron Technology (Bothell, Wash.), and their sequences were verified. The cassettes were supplied both as recombinant plasmid DNA and as *E. coli* clones carrying the recombinant plasmids. Sequences, trace data, and the primers used for sequencing accompanied each cassette. Cassettes are releasable from their vector DNA's by cleavage with a Type IIS restriction enzyme. Cassettes 32 to 35 and 40 to 51 were made by DNA2.0 (Menlo Park, Calif.).

The eight B-series assemblies were constructed from A-series clones that had been cleaved with Not I. It was generally not necessary to gel purify the inserts from the cleaved vector DNA since, without complementary overhangs, they were inactive in subsequent reactions. A-assemblies were taken 3 at a time to make the B-assemblies, except for B62-77, which was constructed from 4 A-assemblies (FIG. 3). The four C-series ¼ genome assemblies were each constructed from 2 of the ⅛-genome B-assemblies as shown in FIG. 3. Clones of correct size were identified, sequence-verified, and stored at −80° C.

Recombinant plasmids bearing the individual cassette DNA inserts were cleaved with the appropriate Type IIS restriction enzymes to release the insert DNA. After phenol-chloroform extraction and ethanol precipitation, the cassettes were used without removing vector DNA. The cassettes were assembled, 4 at a time, in the presence of BAC vector DNA using an in vitro recombination reaction as illustrated in FIG. 3. The steps of the reaction are first, the overlapping DNA molecules are digested with a 3'-exonuclease to expose the overlaps, and then the complementary overlaps are annealed, and the joints are repaired.

To illustrate, the 66-69 assembly was constructed by mixing together equimolar amounts of the 4 cassette DNA's and a linear BAC vector that carries terminal overlaps to cassettes 66 and 69. To generate the overlaps, the BAC was PCR-amplified using primers situated near the BamHI cloning site. Primer 66 (68 bp) contained a 20 bp overlap with the vector to the right of the BamHI site followed by a Not I site and then an overlap with the first 40 bp of cassette 66. Primer 69 (68 bp) overlapped the vector to the left of the site by 20 bp followed by the Not I site and then an overlap with the last 40 bp of cassette 69. The 3'-ends of the mixture of duplex vector and cassette DNA's were then digested to expose the overlap regions using T4 polymerase in the absence of dNTP's. The T4 polymerase was inactivated by incubation at 75° C., followed by slow cooling to anneal the complementary overlap regions. The annealed joints were repaired using Taq polymerase and Taq ligase at 45° C. in the presence of all four dNTP's and nicotinamide adenine dinucleotide (NAD).

As shown in panel A of FIG. 4, four cassette DNA's (66 to 69) are digested from their 3'-termini using the 3'-exonuclease activity of T4 polymerase in the absence of dNTP's to an extent sufficient to expose the regions of overlap (80 bp) between the adjacent fragments. The T4 polymerase is inactivated at 75° C. and complementary overlaps are then annealed by slow cooling. The assembly is then repaired in a separate reaction using Taq polymerase and dNTP's to fill in the gaps, and Taq ligase to close the nicks, thus producing a covalent assembly. As shown in FIG. 4, panel B, a BAC vector is prepared for the assembly reaction by PCR amplification using two primers that overlap 20 bp to either side of the BamHI cloning site, followed by a Not I site, and 40 bp of overlap with cassette 66 or cassette 69. The linear amplification product, after gel purification, is included in the assembly reaction of panel A, such that the desired assembly is a circular DNA containing the 4 cassettes and the BAC DNA as depicted in panel C.

Figure 5:
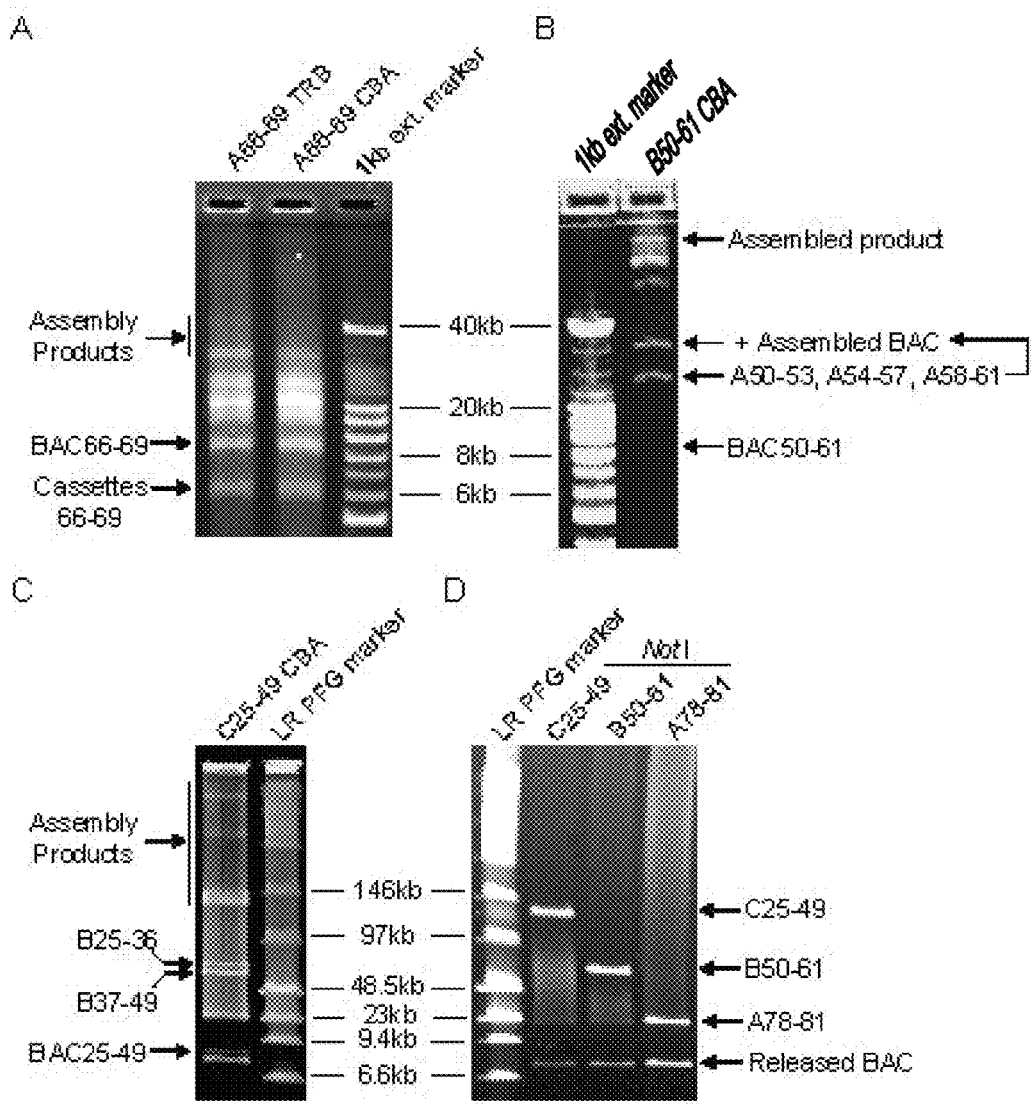
FIGS. 5A-5D show gel electrophoretic analyses of selected examples of A-, B-, and C-series assembly reactions and their cloned products.

A sample of the assembly reaction was subjected to field inversion gel electrophoresis (FIGE) to evaluate the success of the assembly, as shown in FIG. 5. In panel A, the chew-back assembly (CBA) reaction (80 µl) for A66-69 was carried out in a 250 µl PCR tube in a MJ-Research PTC-200 thermocycler and contained 5% PEG-8000, 200 mM Tris-Cl pH 7.5, 10 mM $MgCl_2$, 1mM DTT, 100 µg/ml BSA, 4.8 U of T4 polymerase (NEB), 150 ng each of cassettes 66, 67, 68, and 69 and 150 ng BAC66-69 DNA. Incubation was at 37° C. for 5 min., 75° C. for 20 min., cooled at −6° C./min. to 60° C. and held for 30 min., then cooled at −6° C./min to 4° C. and held. The repair (TRB) reaction (40 µl) contained 10 µl of the chew-back reaction, 40 U Taq DNA ligase (NEB), 1.2 U Taq DNA Polymerase (NEB), 5% PEG-8000, 50 mM Tris-Cl pH 7.5, 10 mM MgC12, 10 mM DTT, 25 µg/ml BSA, 200 µM each dNTP, and 1 mM NAD. Incubation was for 15 min at 45° C. A 5 µl sample of the CBA reaction and a 20 µl sample of the TRB reaction were loaded onto a 0.8% E-GEL™ (Cat. No. G5018-08, BIORAD®) and subjected to FIGE for 3 hours using the U-5 program (2). DNA bands were visualized with the Gel Doc™ (BIO-RAD®). The DNA size standard was the 1 kb extension ladder (INVITROGEN®, Cat. No. 10511-012).

Panel B shows the assembly reaction for B50-61 carried out as described in panel A. The amounts of A50-53, A54-57, and A58-61 DNA's were approximately 450 ng each. BAC50-61 DNA was 150 ng. A sample of the CBA reaction was analyzed as in panel A.

Panel C shows the assembly reaction for C25-49, carried out as described in panel A. Approximately 300 ng, 250 ng, and 60 ng of gel-purified B25-36, B37-49, and BAC25-49 DNA were used respectively. A 10 µl sample of the CBA reaction was loaded onto a BIORAD® "READY AGAROSE MINI GEL™ (Catalog 161-3016) and subjected to FIGE (U-9 program (2)) for 14 hr at 23° C. in a Hoeffer HE33 mini horizontal submarine electrophoresis tray using 1×TAE buffer with 0.5 µg/ml EtBr without circulation. The DNA size standard was the low range PFG marker #N0350S (NEB). Bands were visualized using a Typhoon 9410 Fluorescence Imager (Amersham) with 532 nm excitation and 610 nm emission wavelengths.

Panel D shows sizes of the Not I-cleaved assemblies as determined by FIGE using the U-9 program described in panel C.

Additional samples were electroporated into DH10B™ (INVITROGEN®), EPI300™ (EPICENTRE®), and/or Stb14™ (INVITROGEN®) cells and plated on LB agar plates containing 12.5 µg/ml chloramphenicol. Colonies appeared after 24 to 48 hours. They were picked and grown overnight in 3 ml cultures of LB broth plus chloramphenicol. Plasmid DNA was prepared from 1.5 ml of culture using an alkaline lysis procedure. The DNA was then cleaved with Not I and analyzed by FIGE to verify the correct sizes of the assemblies. Clones with the correct size were frozen in LB medium plus 15% glycerol and stored at −80° C. Some of the cloned assemblies were sequenced to ascertain the accuracy of the synthesis as indicated by bold boxes in FIG. 3.

Figure 6:
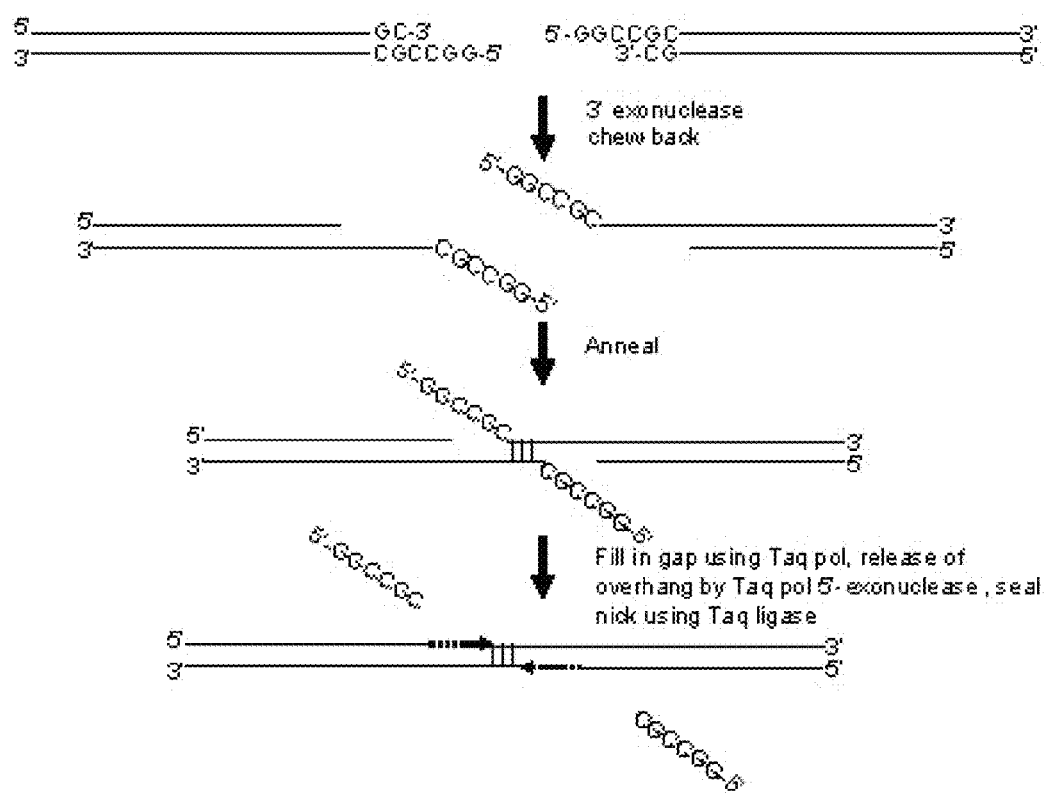
FIG. 6 is a diagram showing repair of annealed junctions containing non-homologous 3' and 5' Not I sequences. The 3'-GC nucleotides are removed during the chew back reaction. In the repair reaction the 5'-GGCCGC Not I overhangs are removed by the 5'-exonuclease activity contained in the Taq polymerase.

The twenty-five A-series assemblies and all the larger assemblies were cloned in the pCC1BAC vector from EPI-CENTRE®. The pCC1BAC clones could be propagated in single copy level in EPI300™ cells and then induced to 10 copies per cell according to the EPICENTRE® protocol. Induced 100 ml cultures yielded up to 200 µg of plasmid DNA. The assembly inserts in the BAC's were immediately flanked on each side by a Not I site such that cleavage efficiently yielded the insert DNA with part of the Not I site attached at each end (the *M. genitalium* genome has no Not I sites). When the Not I-flanked assemblies were used in higher assemblies, the 3'-portion of the Not I site (2 nucleotides) was removed by the chew-back reaction. The 5'-portion of the Not I site produced a 6-nucleotide overhang after annealing, but the overhang was removed during repair by the Taq polymerase 5'-exonuclease activity as shown in FIG. 6.

EXAMPLE 2

In Vivo Recombination in Yeast

Half genome clones could not be propagated in *E. coli* by the in vitro recombination procedure described above. Even the C78-101 clone was difficult to maintain except in STB14™ *E. coli* cells. *S. cerevisiae* was therefore used as a cloning host.

Linear YAC clones are usually constructed by ligation of an insert into a restriction enzyme cloning site (Burke, D. T., et al., *Science*, (1987) 236:806-812. An improvement upon this method uses co-transformation of overlapping insert and vector DNA's into yeast spheroplasts, where they are joined by homologous recombination (FIG. 7A). This produces circular clones and is known as TAR cloning (Larionov, V., et al., *Proc. Natl. Acad. Sci. USA* (1996) 93:491-496). A TAR clone, like a linear YAC, contains a centromere and thus is maintained at chromosomal copy number along with the native yeast genome. The circularity of TAR clones allows them to be readily separated from the linear yeast chromosomes.

Figure 7:
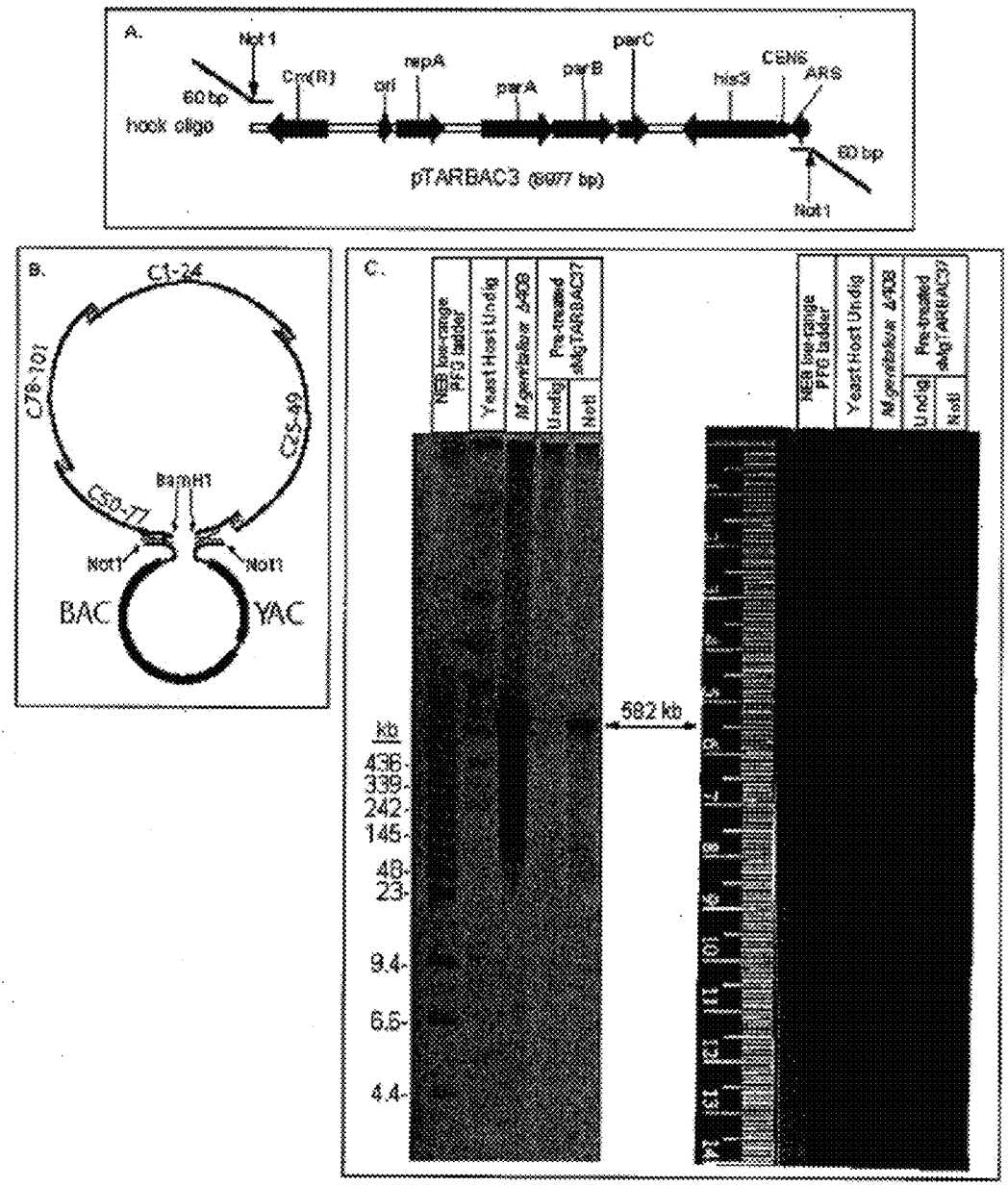
FIGS. 7A-7C show yeast TAR cloning diagram and clone characterization.

Panel A of FIG. 7 shows the vector used for TAR cloning. It contains both BAC and YAC sequences (shown to scale). Recombination of vector with insert occurs at "hooks" added to the TARBAC by PCR amplification. A yeast replication origin (ARS) allows for propagation of clones, as no ARS-like sequences (Newlon, C. S., et al., *Curr. Opin. Genet. Dev.* (1993) 3:752-758) exist in the *M. genitalium* genome. Selection in yeast is by complementation of histidine auxotrophy in the host strain. BAC sequences allow for potential electroporation into *E. coli* of clones purified from yeast.

To assemble ¼ genomes into halves and wholes in yeast, pTARBAC3 vector (Zeng, C., et al., *Genomics* (2001) 11:27-34) was used. This vector contains both YAC and BAC sequences (FIG. 7A). The vector was prepared using a strategy similar to the one described above for BAC vectors. Overlaps were generated at the termini by PCR amplification using primers with 60 bp overlaps to either side of a single cut restriction site within one of the ¼ genomes, followed by a Not I site and 20 bp from the vector termini. The vector was inserted at the intergenic BsmBI site in the third ¼, C50-77. In TAR cloning, recombination is stimulated about twenty-fold at double-stranded breaks (Leem, S. H., et al., *nucleic Acids Res*. (2003) 31:E29. The DNA to be transformed consisted of 6 pieces (vector, 2 fragments of quarter 3, and quarters 1, 2, and 4). To obtain a full-sized genome as an insert in pTARBAC3, a single yeast cell must take up all 6 pieces and assemble them by homologous recombination.

Panel B of FIG. 7 shows assembly of *M. genitalium* JCVI-1.0 ¼ genomes. These were purified from *E. coli*, Not I-digested, and mixed with a TARBAC vector for co-transformation into *S. cerevisiae*, where recombination at overlaps from 60-264 bp combined the six fragments into a single clone. The TARBAC was inserted into the BsmBI site in C50-77.

Transformation of the yeast cells was performed using a published method (Kouprina, N., et al., *Methods Mol. Biol.* (2006) 349:85-101). Yeast cells were harvested from an overnight culture and washed with water, then 1 M sorbitol. Cells were converted to spheroplasts by treatment with Zymolyase™ and β-mercaptoethanol in the presence of 1 M sorbitol. The spheroplasts were washed with sorbitol and resuspended in a buffer containing sorbitol and $CaCl_2$. Spheroplasts equivalent to 5 ml of original yeast culture were incubated in a 200 µl volume at room temperature for 10 min with 10 ng of vector and 120 ng of each ¼ genome. Then 800 µl of 20% polyethylene glycol (PEG) 8000 (US Biochemicals) was added and incubation continued for 10 min. After recovery in rich medium, the transformed cells were selected at 30° C. in top agar on sorbitol plates in the absence of histidine. Transformants were screened first by PCR and then by Southern Blot (FIG. 7C).

In panel C, TAR clones were screened initially by PCR. Clones positive for amplification of all input fragments were then characterized by Southern Blot. Total yeast DNA was prepared in an agarose plug (as per the BIORAD® CHEF DRIII manual protocol), Not I-digested to separate vector from *M. genitalium* sequence, resolved by pulsed-field gel electrophoresis (BIORAD® CHEF DRII or DRIII), transferred by vacuum (BIORAD® Model 785 Vacuum Blotter) to an AMERSHAM® HYBOND®-N+ membrane, probed with a mix of two digoxigenin-labeled (ROCHE®) PCR products that hybridize within the nine *M. genitalium* MgPa repetitive regions, and detected with anti-digoxigenin-AP Fab fragments followed by the fluorescent substrate HNPP (ROCHE®). Desirable clones showed a single band of the same size as chromosomes resolved from an agarose plug of native *M. genitalium* genomes. Shown here is a more detailed digest analysis of the final clone that was sequenced, by pulsed-field electrophoresis. Lanes are as follows: 1) Low-range pulsed field gel marker (NEB), 2) Host yeast strain VL6-48N (Larionov, V., et al., *Proc. Natl. Acad. Sci. USA* (1997) 94:7384-7387, undigested, 3) Native *M. genitalium* ~MG408 (Although this genome is circular, a fraction of the molecules in the agarose plug are broken and these linear molecules electrophorese at about 600 kb, providing a size marker and a blot signal control for the TAR clone), 4) Yeast strain sMgTARBAC37 undigested, and 5) Yeast strain sMgTARBAC37 digested with Not I. Lane 4 shows the topology of the clone, as a 600 kb circle is too large to electrophorese into the gel. A small fraction of the clone is broken and these linear molecules are detected in a faint blot signal. Lane 5, the Not I digested sample shows the size of the insert *M. genitalium* DNA separated from the TARBAC vector.

Clones positive by PCR and Southern Blot were tested for stability by further Southern Blotting of subclones. Based on these two assays, about 10% of the transformant colonies carried a complete synthetic genome. One of these clones, sMgTARBAC37, was selected for sequencing.

TAR cloning was also performed with each of the four sets of two adjacent ¼ genomes, as well as with quarters 1 to 3. DNA's from transformants of these various experiments were isolated and electroporated into *E. coli* (Silverman, G. A., *Methods Mol. Biol.* (1996) 54:65-68). In this way, we obtained BAC clones of the sizes expected for D1-49, D50-101, and assemblies 25-77 and 1-77. Of these, D1-49 was chosen for sequencing and it was correct.

EXAMPLE 3

Recovery of the Synthetic *M. genitalium* Genome from Yeast and Confirmation of its Sequence Agarose plugs of sMgTARBAC37 were prepared according to the Bio-Rad CHEF manual protocol for yeast from a 1.5 L CM-HIS culture grown at 30° C. to an OD of 0.5. The plugs were washed and dialyzed in 1×NEB buffer 4, then incubated overnight at 37° C. with restriction enzymes Rsr II, Fse I, and AsiS I, which cleave yeast but not sMgTAR-BAC37. Digested linear yeast DNA was removed from plugs by agarose gel electrophoresis at 4.5 V/cm for 2 hours. Intact circular sMGTARBAC37 DNA remained in the plug under these conditions. To evaluate the size and purity of the sMgTARBAC37 DNA one plug was incubated with Not I and the DNA in the plug was analyzed by electrophoresis. The gel was stained with SYBR gold.

Figure 8:
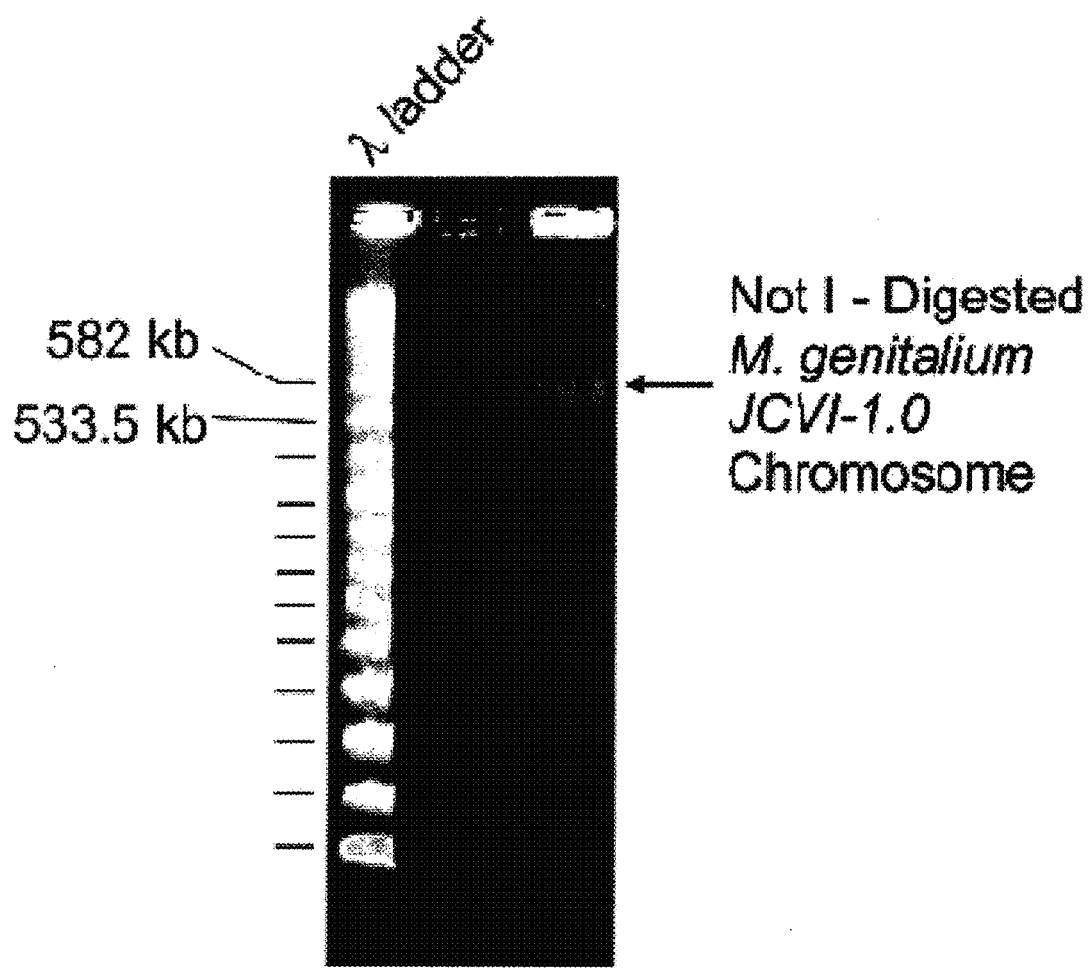
FIG. 8 shows yeast TAR clone size characterization of the complete assembly.

FIG. 8 shows a band of approximately 590 kb with Not I digestion, but no band in the undigested control. DNA from the remaining plugs was used to prepare a library for sequencing. The sMgTARBAC37 DNA was sequenced to X coverage and confirmed to be as designed.

EXAMPLE 4

Assembly of 25 DNA Fragments in Yeast

The DNA fragments employed are overlapping portions of the genome of *Mycoplasma genitalium* and are described in detail in Gibson, D. G., et al., *Science* (2008) 319:1215-1220 (supra).

A. Production of A-series assemblies: Each of the 25 A-series assemblies shown in Table 1 is contained in pCC1BAC™ and was propagated in the EPI300™ *E. coli* strain (EPICENTRE®).

TABLE 1

Summary of the 25 A-series assemblies used in the construction of the *M. genitalium* JCVI-1.1 synthetic genome.

| Assembly | Size | Digestion required to release the vector | Amount overlap to adjacent assembly at 5' end | Amount overlap to adjacent assembly at 3' end |
| --- | --- | --- | --- | --- |
| A1-4 | 23,636 bp | BsmBI | 80 bp | 80 bp |
| A5-8 | 26,166 bp | NotI | 80 bp | 80 bp |
| A9-12 | 23,872 bp | BsmBI | 80 bp | 80 bp |
| A13-16 | 23,653 bp | SalI and NotI | 80 bp | 80 bp |
| A17-20 | 23,312 bp | NotI | 80 bp | 80 bp |

TABLE 1-continued

Summary of the 25 A-series assemblies used in the construction of the *M. genitalium* JCVI-1.1 synthetic genome.

| Assembly | Size | Digestion required to release the vector | Amount overlap to adjacent assembly at 5' end | Amount overlap to adjacent assembly at 3' end |
|---|---|---|---|---|
| A21-24 | 23,211 bp | NotI | 80 bp | 80 bp |
| A25-28 | 24,992 bp | NotI | 80 bp | 80 bp |
| A29-32 | 26,257 bp | NotI | 80 bp | 209 bp |
| A33-36 | 20,448 bp | NotI | 209 bp | 80 bp |
| A37-41 | 25,706 bp | NotI | 80 bp | 257 bp |
| A42-45 | 19,223 bp | NotI | 257 bp | 257 bp |
| A46-49 | 19,895 bp | NotI | 257 bp | 257 bp |
| A50-53 | 24,390 bp | NotI | 257 bp | 80 bp |
| A54-57 | 24,789 bp | NotI | 80 bp | 80 bp |
| A58-61 | 24,534 bp | NotI | 80 bp | 80 bp |
| A62-65 | 25,055 bp | NotI | 80 bp | 80 bp |
| A66-69 | 23,128 bp | NotI | 80 bp | 80 bp |
| A70-73 | 23,345 bp | NotI | 80 bp | 80 bp |
| A74-77 | 21,396 bp | NotI | 80 bp | 165 bp |
| A78-81 | 22,320 bp | NotI | 165 bp | 360 bp |
| A82-85 | 23,460 bp | NotI | 360 bp | 85 bp |
| A86-89 variant | 34,950 bp | NotI | 85 bp | 80 bp |
| A90-93 | 23,443 bp | NotI | 80 bp | 80 bp |
| A94-97 | 24,511 bp | NotI | 80 bp | 80 bp |
| A98-101 | 17,372 bp | NotI | 80 bp | 80 bp |

A variant of A86-89 as compared to the published description was used, which has a vector inserted within a nonessential gene. The vector contains a histidine auxotrophic marker, a centromere and an origin of replication for selection and maintenance in yeast. The inclusion of a vector with yeast propagation elements permits evaluation of results of assembly.

The cloning system allows for 10 copies or more of these BACs per cell. *E. coli* strains with these 25 assemblies were inoculated into 150 ml LB plus 12.5 µg/ml chloramphenicol and 1× induction solution (EPICENTRE®) and incubated at 37° C. for 16 hours. The cultures were harvested and the BACs were purified using QIAGEN®'s HISPEED® Plasmid Maxi Kit. DNA was eluted using 500 µl TE buffer. Restriction digestions to release the fragments from their BACs were carried out at 37° C. for 16 hours and then terminated by phenol-chloroform extraction and ethanol precipitation. The products were dissolved in TE buffer to a final concentration of 120 ng/µl.

Following digestion, each of the 25 assemblies contains at least 80 bp of overlapping sequence with the intended adjacent molecule at either end.

B. Yeast spheroplast transformation: Yeast cells were treated with ZYMOLYASE™ to weaken the cell wall, and then made competent to take up foreign DNA by treatment with PEG and $CaCl_2$, using the VL6-48N yeast strain (Kouprina, N., et al., supra). Cells were grown to an $OD_{600}$ of 1.3 (~5×10$^7$ cells/ml) prior to preparation of yeast spheroplasts. The digested 25 A-series assemblies were pooled by adding 96 ng (0.8 µl of 120 ng/µl) of each then mixed with ~10$^8$ yeast spheroplasts. Equal amounts, ~100 ng or ~4×10$^9$ genome equivalents, of each digested piece from paragraph A were pooled together without gel purification. Approximately 10$^8$ yeast spheroplasts were added to this DNA pool and yeast transformation Was performed (Kouprina, N., et al., *Nat. Protoc.* (2008) 3:371-377). This amounts to ~40 *M. genitalium* genome equivalents, or ~1000 DNA molecules (40×25) per yeast spheroplast. Following transformation, yeast spheroplasts were regenerated and selected on complete supplemental medium without histidine (CSM-His) plus adenine and 1M sorbitol agar plates for 3 days at 30° C.

Following incubation for 3 days at 30° C. on selective medium, approximately 800 colonies were obtained. Individual colonies were then transferred onto CSM-His agar plates as small patches and incubated for 2 days at 30° C. Once screened and confirmed to have the desired assembly, individual colonies from these plates were also analyzed.

The overall process is diagrammed in FIG. 9. As shown, yeast cells were transformed with the 25 different overlapping A-series DNA segments (~17 kb to ~35 kb each) comprising the *M. genitalium* genome. In order to assemble these into a complete genome, a single yeast cell must take up at least one representative of the 25 different DNA fragments and incorporate each into the nucleus, where homologous recombination takes place. The assembled genome, labeled JCVI-1.1 in the figure, is 590,011 bp including the vector sequence (triangle) shown internal to A86-89. As noted above, yeast propagation elements contained within the vector are an origin of replication (ARSH4), a centromere (Cen6), and a histidine selectable marker (His3).

C. Multiplex PCR analysis: DNA was extracted from the cultured yeast cells using The CHARGESWITCH® Plasmid Yeast Mini Kit (INVITROGEN®, catalog number CS10203) according to the provided manual. Multiplex PCR was carried out in 10 µl reactions using a master mix consisting of a PCR buffer, a dNTP mixture, and HOT-STARTAQ™ DNA polymerase (QIAGEN®, catalog number 206143). Two microliters of DNA, and 1 µl of a 10× primer stock, containing 20 oligos at 5 µM each, was added to each reaction. Cycling parameters were 94° C. for 15 min, then 35 cycles of 94° C. for 30 sec, 45° C. (primer set 1) or 55° C. (primer sets 2-4) for 90 sec, followed by a single 72° C. incubation for 3 minutes. Two microliters of each reaction was loaded onto a 2% E-GEL® (INVITROGEN®) and 72V was applied for 30 minutes. Bands were visualized using an AMERSHAM® TYPHOON® 9410 Fluorescence Imager.

We first screened for yeast cells that took up all 25 pieces. Forty primer pairs, producing amplicons ranging in size from 100 bp to 1075 bp, were designed such that they can produce 10 amplicons in each of 4 individual multiplex PCR reactions. Multiplex primer sets 1 and 2 were previously described (Gibson, D. G., et al., supra). The 40 amplicons are positioned around the *M. genitalium* genome approximately every 15 kb. All 25 segments are required to be present to give rise to all 40 amplicons by PCR, thus giving a very good indication that all 25 pieces were incorporated into a yeast cell. This is diagrammed in FIGS. 10A-10B. As shown in FIG. 10A, 40 amplicons were designed such that 10 products could be produced in 4 separate multiplex PCR reactions (Set 1-Set 4). As diagrammed in FIG. 10B, the 40 sets of primers each amplifies a small portion of the *M. genitalium* genome approximately once every 15 kb. Each of the 25 segments (arrows) provides primer binding sites for at least one of the 40 amplicons (shown as lines). Ten individual colonies were transferred to a single selective plate as small patches. Following incubation for 2 days at 30° C., approximately $10^7$ cells from each of these 10 patches were scraped into 1 ml of water. Using multiplex primer set 1 and DNA extracted from these 10 clones, multiplex PCR was performed and analyzed by gel electrophoresis. Clones 1 and 4 produced all 10 amplicons. Amplicon 1-h gave a weak signal that could be observed when the exposure time was increased (data not shown). This PCR analysis confirmed the presence of 10 of the 25 A-series assemblies in clones 1 and 4.

PCR products range in size from 100 bp to 1075 bp and can be easily separated by electrophoresis on 2% agarose gels. In the results shown in FIG. 10C, DNA was extracted from 10 yeast clones and multiplex PCR, with primer set one, was performed. Clones 1 and 4 (c1 and c4) efficiently generated 9 of the 10 predicted amplicons. Amplicon 1-h could be observed when the signal emanating from the gel was increased.

D. Detailed analysis of clone 4. Using multiplex primer sets 1-4, multiplex PCR was performed and analyzed by gel electrophoresis. With the exception of amplicon 1-h, all 40 PCR products were efficiently generated from DNA extracted from clone 4. This confirms the presence of all 25 A-series assemblies (compare to FIG. 10B). A70-73 is represented by amplicons 1-h and 3-h. Although amplicon 1-h is generated at lower levels compared to the other amplicons, amplicon 3-h is efficiently produced, providing strong evidence for the presence of A70-73 in clone 4. Clone 4 was selected for further analysis. In the results shown in FIG. 10D, multiplex PCR was performed on clone 4 using all 4 primer sets. With the exception of amplicon 1-h, all 40 amplicons can be efficiently generated from this clone. In lanes labeled "L", the 100 bp ladder (NEB) was loaded and sizes are indicated.

E. Restriction analysis of the JCVI-1.1 synthetic *M. genitalium* genome: DNA was prepared from clones in 1% agarose using the BIORAD® Yeast DNA Plug Kit and according to the instruction manual provided (catalog number 170-3593). Following the completion of this protocol, plugs were submerged in 1×TAE in a horizontal submarine electrophoresis tray and 5.4 V/cm was applied for 2 hours. The plugs were then removed and stored in TE buffer. Plugs were digested according to the BIORAD® manual with EagI, BssHII, or AatII (restriction enzymes and buffers were supplied by NEB). Following an incubation at 37° C. for 16 hours, equal amounts of each plug (approximately 20 μl) were loaded onto 1% BIORAD® READY AGAROSE MINI GELS™ then subjected to field-inversion gel electrophoresis (FIGE) for 14 hours at 23° C. in a HOEFER® HE 33 mini horizontal submarine electrophoresis tray using 1×TAE buffer with 0.5 μg/ml ethidium bromide without circulation using the U-2 program. The parameters for FIGE U-2 are forward 90 V, initial switch 5.0 sec, final switch 30 sec, with linear ramp and reverse 60 V, initial switch 5.0 sec, final switch 30 sec. Bands were visualized using a TYPHOON® 9410 Fluorescence Imager (AMERSHAM®) with 532 nm excitation and 610 nm emission wavelengths.

To verify that all 25 pieces were assembled into the complete genome in clone 4, DNA was prepared from these yeast cells in agarose plugs for restriction analyses as described above. As a negative control, DNA was also extracted from the untransformed host strain. To enrich for the circular genome in the plugs, most of the linear yeast chromosomal DNA was removed by constant voltage electrophoresis. After digestion with EagI, BssHII, and AatII, five restriction fragments predicted by these digests for a complete genome assembly are observed when the digested plugs are subjected to field-inversion gel electrophoresis as shown in FIG. 11C. The host yeast control shows none of these bands and only a smear of DNA smaller than ~150 kb is observed. This smear would obscure the other predicted fragments of the assembled genome. Together with the multiplex PCR analyses (FIG. 10), these results indicate that clone 4 has an assembled JCVI-1.1 synthetic genome, having taken up at least 25 overlapping segments of DNA and recombining them in vivo.

Figure 11:
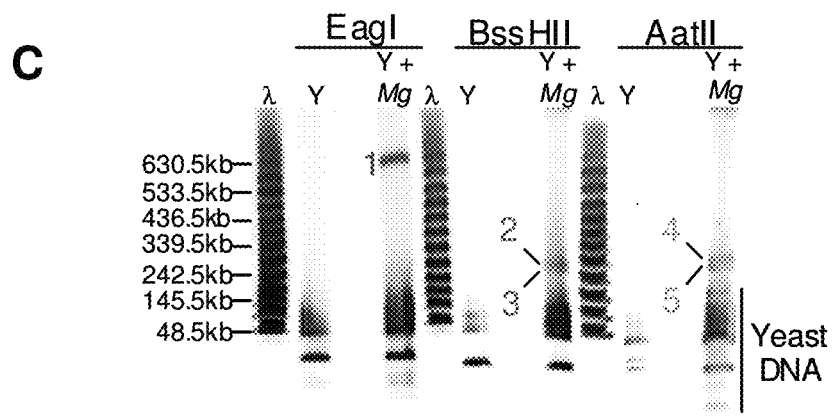
FIGS. 11A-11C show the results of validation of a completely intact *M. genitalium* genome by restriction analysis.
Figure 12:
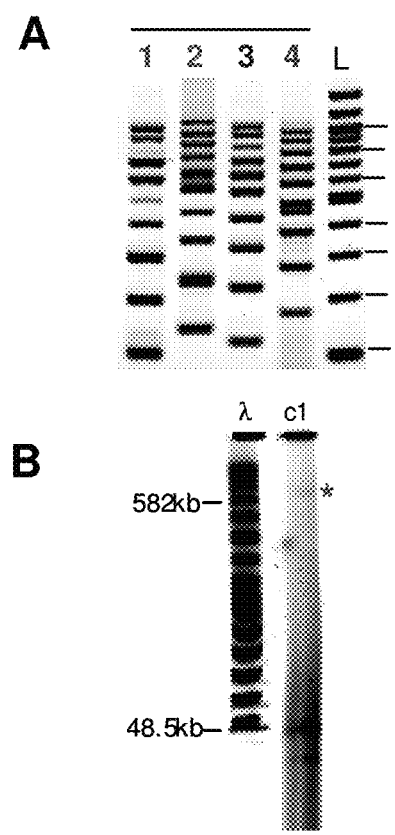
FIGS. 12A-12B show further analysis of clone 1 examined in FIG. 11.

Clone 1 gave a similar pattern to clone 4 when multiplex PCR products, amplified using primer set 1, were analyzed (FIG. 10C). Therefore, we further analyzed clone 1. Using the 4 multiplex PCR primer sets shown in FIG. 10, all 40 amplicons are observed for clone 1, and following an EagI digest as shown in FIG. 11, the predicted 590 kb band is present as shown in FIG. 12.

In FIG. 12A, multiplex PCR was performed on DNA extracted from clone 1 using all 4 primer sets as in FIG. 10. All 40 amplicons are observed following electrophoresis on a 2% agarose gel. In FIG. 12B, DNA was prepared from clone 1 in agarose plugs then digested with EagI and analyzed as in FIG. 11. The predicted 590 kb band can be observed (denoted by *) following field-inversion gel electrophoresis on a 1% agarose gel.

Thus 2 out of the 10 yeast clones examined contain a complete genome.

The invention claimed is:

1. A method for the synthesis of a nucleic acid molecule of a predetermined nucleotide sequence, comprising:
   a) providing a plurality of cassettes of 2-10 kb in length, each cassette containing a nucleotide sequence of a portion of the nucleic acid molecule, wherein the cassettes contain overlapping portions of the nucleotide sequence of the nucleic acid molecule and wherein the cassettes, if combined according to the overlapping portions, provide the complete nucleotide sequence of the nucleic acid molecule;
   b) joining said cassettes in vitro to obtain a plurality of resulting subsets of from about 15 kb to about 200 kb or 50-500 kb in size; and wherein said subsets contain overlapping portions of the nucleic acid molecule of at least 80 bp and wherein the subsets, if assembled according to the overlapping portions, would provide the complete nucleotide sequence of the nucleic acid molecule; and
   c) transfecting yeast host cells with a mixture of fragments of DNA comprising 10 or more subsets, and assembling the fragments of DNA comprising the 10 or more subsets in vivo in the yeast to obtain the nucleic acid molecule of predetermined nucleotide sequence, wherein one of the fragments of DNA includes an origin of replication operable in yeast.

2. The method of claim 1, wherein a step b) and/or step c) is repeated at least once.

3. The method of claim 1, wherein said nucleic acid molecule of predetermined nucleotide sequence of step c) includes a centromere and/or a selectable marker.

4. The method of claim 1, wherein one of the fragments of DNA is a vector and said vector comprises the origin of replication.

5. The method of claim 4, wherein said vector comprises a centromere and/or a selectable marker.

6. The method of claim 1, wherein one or more cassettes in step a) contains a watermark.

7. The method of claim 1 wherein the nucleic acid molecule of predetermined sequence is a synthetic genome.

8. The method of claim 1 wherein two of the fragments each comprise a telomere at one terminus.

* * * * *

SEQUENCE LISTING

<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: consensus sequence
<220> FEATURE:
<221> NAME/KEY: misc_feature

```
<222> LOCATION: (1)...(1)
<223> OTHER INFORMATION: n = t or a
<220> FEATURE:
<221> NAME/KEY: misc_feature
<222> LOCATION: (6)...(6)
<223> OTHER INFORMATION: n = t or c
<220> FEATURE:
<221> NAME/KEY: misc_feature
<222> LOCATION: (7)...(7)
<223> OTHER INFORMATION: n = a or g
<220> FEATURE:
<221> NAME/KEY: misc_feature
<222> LOCATION: (11)...(11)
<223> OTHER INFORMATION: n = t or a

<400> SEQUENCE: 1
ntttannttt n                                                                11
```